(12) United States Patent
Liu et al.

(10) Patent No.: US 11,630,174 B2
(45) Date of Patent: Apr. 18, 2023

(54) MAGNETS AND MAGNETIC RESONANCE IMAGING SYSTEMS

(71) Applicant: Magnetica Limited, Eagle Farm (AU)

(72) Inventors: Feng Liu, Eagle Farm (AU); Riyu Wei, Eagle Farm (AU); Ewald Weber, Eagle Farm (AU)

( * ) Notice: Subject to any disclaimer, the term of this patent is extended or adjusted under 35 U.S.C. 154(b) by 60 days.

(21) Appl. No.: 17/427,849

(22) PCT Filed: Nov. 22, 2019

(86) PCT No.: PCT/AU2019/051285
§ 371 (c)(1),
(2) Date: Aug. 2, 2021

(87) PCT Pub. No.: WO2020/163892
PCT Pub. Date: Aug. 20, 2021

(65) Prior Publication Data
US 2022/0128638 A1  Apr. 28, 2022

(30) Foreign Application Priority Data
Feb. 12, 2019  (AU) ................................ 2019900450

(51) Int. Cl.
| G01R 33/38 | (2006.01) |
| G01R 33/3815 | (2006.01) |
| G01R 33/00 | (2006.01) |
| G01R 33/30 | (2006.01) |
| G01R 33/421 | (2006.01) |
| A61B 5/055 | (2006.01) |

(52) U.S. Cl.
CPC ..... G01R 33/3815 (2013.01); G01R 33/0005 (2013.01); G01R 33/307 (2013.01); G01R 33/4215 (2013.01); A61B 5/055 (2013.01)

(58) Field of Classification Search
CPC ............ G01R 33/3815; G01R 33/0005; G01R 33/307; G01R 33/4215
See application file for complete search history.

(56) References Cited

U.S. PATENT DOCUMENTS

| 2006/0055406 | A1 | 3/2006 | Lvovsky et al. |
| 2007/0018648 | A1 | 1/2007 | Doddrell et al. |
| 2010/0079144 | A1* | 4/2010 | Crozier .............. G01R 33/3815 |
| | | | 324/319 |
| 2017/0242084 | A1* | 8/2017 | Wei .......................... H01F 6/06 |

FOREIGN PATENT DOCUMENTS

CN  103499797 B  3/2016

* cited by examiner

*Primary Examiner* — G. M. A Hyder
(74) *Attorney, Agent, or Firm* — Womble Bond Dickinson (US) LLP

(57) ABSTRACT

A magnet suitable for use in a Magnetic Resonance Imaging (MRI) system. The magnet includes a magnet body having a bore extending therethrough along an axis of the body and a primary coil structure having at least four primary coils positioned along the axis. A first end coil is adjacent a first end of the bore of the magnet and a second end coil is adjacent a second end of the magnet. The first end coil and the second end coil are spaced apart by no more than 1000 mm and an imaging region produced by the primary coils is of a disk-type.

20 Claims, 19 Drawing Sheets

DSV size: 10cm(Z-) X 32cm (R-)

10 ppm (peak-peak) contours

MAGNETS AND MAGNETIC RESONANCE IMAGING SYSTEMS

This application is a U.S. national stage application of the PCT International Application No. PCT/AU2019/051285 filed on Nov. 22, 2019, which claims the benefit of foreign priority of Australian patent application No. 2019900450 filed on Feb. 12, 2019, the contents all of which are incorporated herein by reference.

The present disclosure relates to magnets for use in magnetic resonance imaging and Magnetic Resonance Imaging (MRI) systems. In particular, an invention of the disclosure relates to disk-type magnetic resonance imaging systems.

BACKGROUND

Any references to methods, apparatus or documents of the prior art are not to be taken as constituting any evidence or admission that they formed, or form, part of the common general knowledge.

Magnetic resonance imaging was introduced in the 1980s, and has developed into a major medical imaging modality.

Clinical MRI depends for its success on the generation of strong and uniform magnetic fields. MRI machines are designed to generate a static magnetic field that is required to be substantially homogeneous over a predetermined region, known in the art as the "imaging region", "diameter spherical imaging volume" or "DSV". Deviations from homogeneity of the static magnetic field over the DSV are typically required to be less than 20 parts per million peak-to-peak (or 2 parts per million rms).

MRI equipment has undergone a number of refinements since the introduction of the first closed cylindrical systems. In particular, improvements have occurred in quality/resolution of images through improved signal to noise ratios and introduction of high and ultra-high field magnets. Improved resolution of images, in turn, has led to MRI being a modality of choice for an increasing number of specialists for both structural anatomical and functional human MRI imaging.

The basic components of a typical magnetic resonance system for producing diagnostic images for human studies include a main magnet (usually a superconducting magnet which produces the substantially homogeneous static magnetic field (the $B_0$ field) in the DSV), one or more sets of shim coils, a set of gradient coils, and one or more RF coils. Discussions of MRI, can be found in, for example, Haacke et al., *Magnetic Resonance Imaging: Physical Principles and Sequence Design*, John Wiley & Sons, Inc., New York, 1999. See also Crozier et al., U.S. Pat. No. 5,818,319, Crozier et al., U.S. Pat. No. 6,140,900, Crozier et al., U.S. Pat. No. 6,700,468, Dorri et al., U.S. Pat. No. 5,396,207, Dorri et al., U.S. Pat. No. 5,416,415, Knuttel et al., U.S. Pat. No. 5,646,532, and Laskaris et al., U.S. Pat. No. 5,801,609, the contents of which are incorporated herein in their entireties.

Conventional, whole body MRI magnets are typically cylindrical around 1.6-2.0 meters in length with free-bore diameters in the range of 0.8-1.0 meters. Normally the magnet is symmetric such that the midpoint of the DSV is located at the geometric centre of the magnet's structure along its main axis. The uniformity of the axial component of the magnetic field in the DSV is often analyzed by a spherical harmonic expansion.

The typical aperture of a conventional MRI machine after the addition of ancillary components (gradients and radiofrequency coils) is a cylindrical space having a diameter of about 0.6-0.8 meters, i.e., just large enough to accept the subject's shoulders, and a length of about 2.0 meters or more. Not surprisingly, many people suffer from claustrophobia when placed in such a space. Also, the large distance between the portion of the subject's body which is being imaged and the end of the magnet system means that physicians cannot easily assist or personally monitor a subject during an MRI procedure. Therefore, there is a need for a short or compact magnet system in clinical applications.

The challenge in designing such a high-field system is maintaining both the field homogeneity and size of the DSV using the currently available, cost-effective, superconducting technology. The magnet performance is largely related to the bore size in both axial and radial directions. Short or compact magnets are very difficult to design and build. This is mainly because the dense coil structure produced by conventional designs will lead to unacceptable peak field values and stress for the superconducting coil bundles. Normally, an engineering compromise in DSV size has to be made relative to the size of the magnet.

In addition to its effects on the subject, the size of the magnet is a primary factor in determining the cost of an MRI machine, as well as the costs involved in the installation of such a machine. Another important consideration is the volume of helium needed to maintain the system at cryogenic temperatures. Due to their large size, such whole body magnets are expensive for use in producing images of small sizes of objects, such as, heads, extremities and neonates, etc.

In order to be used safely, MRI machines often need to be shielded so that the magnetic fields surrounding the machine at the location of the operator are below regulatory agency-specified exposure levels. By means of shielding, the operator can be safely sited much closer to the magnet than in an unshielded system. Longer magnets require more shielding and larger shielded rooms for such safe usage, thus leading to higher costs.

Thus, there is a need for a shorter or more compact magnet system in clinical applications.

OBJECT

It is an aim of this disclosure to provide a magnet or magnetic resonance imaging system which overcomes or ameliorates one or more of the disadvantages or problems described above, or which at least provides a useful commercial alternative.

Other preferred objects of the present invention will become apparent from the following description.

SUMMARY

In a first aspect, the invention resides in a magnetic resonance imaging system for producing magnetic resonance images through moving human subjects. The system comprises a magnet that produces a disk-type homogeneous magnetic field region; a gradient coil; and a radio frequency (RF) coil.

In another aspect, the invention resides in method for moving a patient through a magnetic resonance imaging system to conduct imaging during movement and/or at multiple positions.

In another aspect, the invention resides in a magnet suitable for use in a Magnetic Resonance Imaging (MRI)

system, the magnet having a magnet body having a bore extending therethrough along an axis of the body, the magnet comprising:

a primary coil structure having at least four primary coils positioned along an axis, including a first end coil adjacent a first end of the bore of the magnet and a second end coil adjacent a second end of the magnet, wherein the first end coil and the second end coil are spaced apart by no more than 1000 mm, and wherein an imaging region produced by the primary coils is of a disk-type.

Preferably, the disk-type imaging region has an axial diameter (Dz) and a radial diameter (Dr), wherein the axial diameter is less than the radial diameter. More preferably, a ratio of the axial diameter to the radial diameter of the disk-type imaging region is equal to or less than 0.75.

Preferably, a diameter of the imaging region along an x-axis is between 100 mm and 500 mm. Preferably, a diameter of the imaging region along a y-axis is between 100 mm and 500 mm. Preferably, a diameter of the imaging region along a z-axis is between 20 mm and 350 mm. In a preferred embodiment, the imaging region has dimensions of 250 mm(x−)×250 mm(y−)×40 mm(z−). In another preferred embodiment, the imaging region has dimensions of 320 mm(x−)×320 mm(y−)×100 mm(z−). In another preferred embodiment, the imaging region has dimensions of 450 mm(x−)×450 mm(y−)×100 mm(z−). In yet another preferred embodiment, the imaging region has dimensions of 300 mm(x−)×300 mm(y−)×100 mm(z−).

Preferably, the first end coil and the second end coil are spaced apart by between 300 mm and 1000 mm.

Preferably, the primary coil structure has between four primary coils and eight primary coils. Preferably, the primary coil structure has four primary coils, five primary coils, six primary coils or seven primary coils.

Preferably, each of the primary coils has a same current polarity. Alternatively, one of the at least four primary coils adjacent the second end coil has an opposite current polarity to the second end coil.

Preferably, the primary coil structure is symmetric relative to an axial centre of the imaging region. Alternatively, the primary coil structure is asymmetric relative to an axial centre of the imaging region.

Preferably, the magnet body and bore are cylindrical, conical, frustoconical or stepped. Preferably, the magnet body and bore comprise at least one cylindrical portion. Preferably, a cylindrical portion adjoins a frustoconical portion. Alternatively, or additionally, a first cylindrical portion having a diameter adjoins a second cylindrical portion having a diameter, wherein the diameter of the first cylindrical portion is greater than the diameter of the second cylindrical portion. Preferably, a plurality of frustoconical portions and/or cylindrical portions define a stepped-diameter bore.

Preferably, an inner diameter of the bore is between 200 mm and 1100 mm. In a preferred embodiment, the bore is frustoconical having a largest diameter of 820 mm and a smaller diameter of 282 mm.

Preferably, the primary coils are cylindrical, conical, frustoconical or stepped.

Preferably, the magnet comprises a stepped diameter bore having at least one primary coil located about a first step of the stepped diameter bore and at least one primary coil located about a second step of the stepped diameter bore.

Preferably, the magnet is capable of producing a magnetic field of at least 1.0 Tesla and more preferably a magnetic field of at least 3.0 Tesla. Preferably, the magnetic field is substantially homogenous over a predetermined imaging region.

Preferably, the imaging region has an external surface defined by a computed variation of a longitudinal magnetic field relative to the longitudinal magnetic field at an imaging centre of less than 20 parts per million peak-to-peak.

In yet another aspect, the invention resides in a magnetic resonance imaging system having a magnet suitable for use in a Magnetic Resonance Imaging (MRI) system, the magnet having a bore extending along an axis of the magnet, the magnet comprising:

a primary coil structure having at least four primary coils positioned along an axis, including a first end coil adjacent a first end of the bore of the magnet and a second end coil adjacent a second end of the magnet, wherein the first end coil and the second end coil are spaced apart by no more than 1000 mm, and wherein an imaging region produced by the primary coils is of a disk-type.

Preferably, the magnet or the MRI system further comprises a shield coil structure. Preferably, the shield coil structure is located around the primary coil structure (i.e. has a larger diameter than the primary coil structure). Preferably, the shield coil structure comprises at least one shield coil having a greater diameter than the primary coils. Preferably, the shield coil structure is located radially outwardly of the primary coil structure.

Preferably, the shield coil structure has at least two shield coils.

Preferably, each of the shield coils carry current in a direction opposite to a direction of current in the first and second end coils of the primary coil structure.

Preferably, each of the shield coils are superconducting or ferromagnetic.

Preferably, in use, the shield coils tailor the magnetic fields within the imaging region.

Preferably, the magnet or the MRI system further comprises a gradient coil structure comprising a primary coil layer and a shield coil layer. Preferably, a length of the primary coil layer of the gradient coil structure is less than a length of the shield coil layer of the gradient coil structure. More preferably, the length of the primary coil layer of the gradient coil structure is significantly less than the length of the shield coil layer of the gradient coil structure. Advantageously, the shield coil layer can be closer to the primary coil layer to reduce the gradient coil thickness while still maintaining good shielding performance.

Preferably, the gradient coil structure is located within a gradient body located within the magnet. Preferably, the gradient body is located between the bore and the magnet body.

Preferably, the magnet or the MRI system further comprises one or more Radio Frequency (RF) coils located between the gradient coil structure and the bore. Preferably, the RF coils are frustoconical and/or cylindrical confirming to a shape of the bore. Preferably, the RF coils are located on an inner surface of the gradient body surrounding the bore.

Preferably, the system further comprises one or more shim pockets. Preferably, the shim pockets are frustoconical and/or cylindrical. Preferably, a shim portion is located in each shim pocket. Preferably, the shim portion comprises ferrous or ferromagnetic material. Preferably, each primary coil has an associated shim pocket and shim portion having a shape conforming to the shape of the magnet body and/or the bore. Preferably, the shim portions passively shim the imaging region to achieve a preferred field ($B_0$) homogeneity level. Preferably, the shim device is located between the primary coil structure and the shield coil structure. In some embodiments, the shim device is located outside of the shield coil structure. Preferably, the shim device is located between the magnet and gradient coils.

Preferably, a length of the bore is between 250 mm and 1000 mm. In some preferred embodiments, the length of the bore is 300 mm, 570 mm, 600 m, 800 mm or 900 mm.

Preferably, a size of a five Gauss line is between 1.5 m and 6 m in a radial direction and between 2.5 m and 9 m in an axial direction. In some preferred embodiments, the five Gauss line has dimensions of:
- 3 m in the radial direction and 5 m in the axial direction; or
- 4.6 m in the radial direction and 7.9 m in the axial direction; or
- 4.8 m in the radial direction and 7.0 m in the axial direction; or
- 4.3 m in the radial direction and 6.5 m in the axial direction.

Preferably, the magnetic resonance imaging system comprises a movable platform or portion adapted to support a patient. Preferably, the movable platform or portion is adapted to move through the bore of the magnetic resonance imaging system.

In another form, the invention resides in a method of magnetic resonance imaging scanning, the method comprising the steps of:
moving a platform bearing a patient through a magnetic resonance imaging system, the magnet resonance imaging system having a magnet as described above.

According to a further aspect of the present invention there is provided a magnet suitable for use in a Magnetic Resonance Imaging (MRI) system, the magnet having a magnet body with a bore extended therethrough along an axis of the body, the magnet comprising:
a primary coil structure having at least four primary coils positioned coaxially along the axis, including a first end coil adjacent a first end of the bore and a second end coil adjacent a second end of the bore, the primary coil structure arranged to generate a substantially homogenous disk shaped imaging region within the bore.

Further features and advantages of the present invention will become apparent from the following detailed description.

BRIEF DESCRIPTION OF THE DRAWINGS

By way of example only, preferred embodiments of the invention will be described more fully hereinafter with reference to the accompanying figures, wherein.

DETAILED DESCRIPTION OF THE PREFERRED EMBODIMENTS

Figure 1:
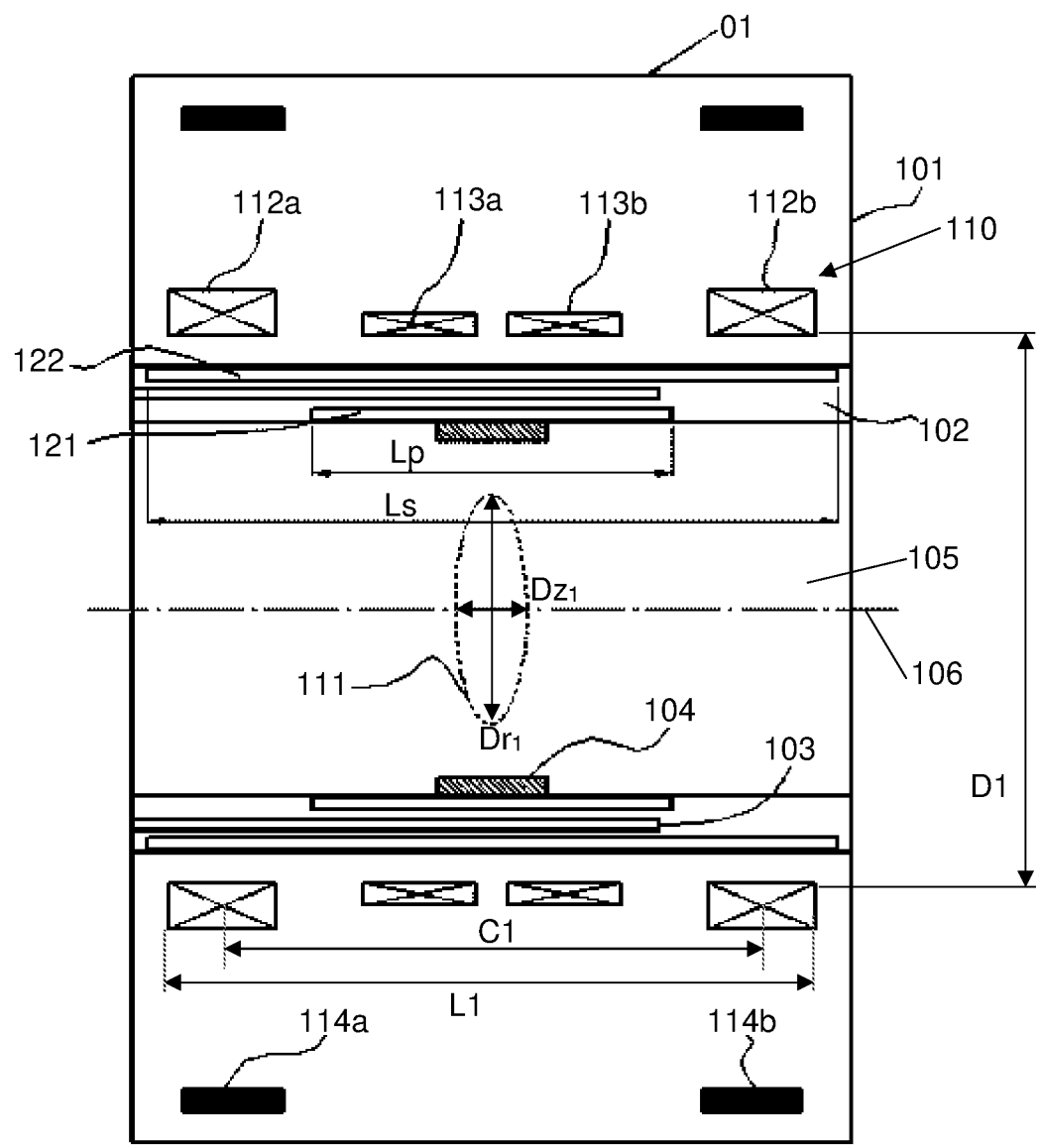
FIG. 1 illustrates a schematic cross-section view of a magnetic resonance imaging system according to a first embodiment of the present invention.

Referring to FIG. 1 there is illustrated a magnetic resonance imaging system 01. The system 01 includes a magnet 101 being a superconducting magnet, a gradient body 102, passive shim pockets 103, a RF coil 104 and a bore 105 extending axially through the magnet 101 parallel to longitudinal axis 106.

The bore 105 of the magnet 101 has a cold bore length L1 (preferably between 250 mm and 1000 mm) and an inner bore diameter D1

The magnet 101 is symmetric with respect to the centre of the Diameter of Spherical Volume (DSV)/imaging region and comprises a primary coil structure 110 having four primary coils: a first end coil 112a, a second end coil 112b, and two middle coils 113a, 113b located between the first end coil 112a and second end coil 112b. Each of the coils 112a, 112b, 113a, 113b have the same (positive) polarity. The respective end coils 112a, 112b, located at opposite ends of the bore 105 are spaced apart by distance C1, which is preferably between 300 mm and 1000 mm. It will be appreciated that the distance between the end coils 112a, 112b is measured from a centre of one coil to a centre of the other coil.

The system 01 also includes two shield coils 114a and 114b with opposite (negative) polarity to the polarity of the primary coils 112a, 112b, 113a, 113b, which produces a disk-type DSV 111 having an axial diameter $Dz_1$ less than the radial diameter $Dr_1$, where the ratio of the axial diameter $Dz_1$ to the radial diameter $Dr_1$ of the DSV 211 is equal to or less than 0.75.

A gradient body 102 is located within the magnet 101. Inside the gradient body 102, there is located a primary gradient coil layer 121 and a shield gradient coil layer 122, generating three orthogonal gradient fields in three orthogonal z, x and y axes.

The electric current directions in the shield gradient coils of the shield gradient coil layer 122 are opposite to those in the relevant primary gradient coils of the primary gradient coil layer 121. The length (Lp) of the primary gradient coil layer 121 is significantly shorter than the length (Ls) of the shield gradient coil layer 122, allowing closer radial distance between the primary and shield layers while still maintaining good shielding performance. The RF coil 104 is also short and therefore efficient due to a shorter DSV.

Figure 1A:
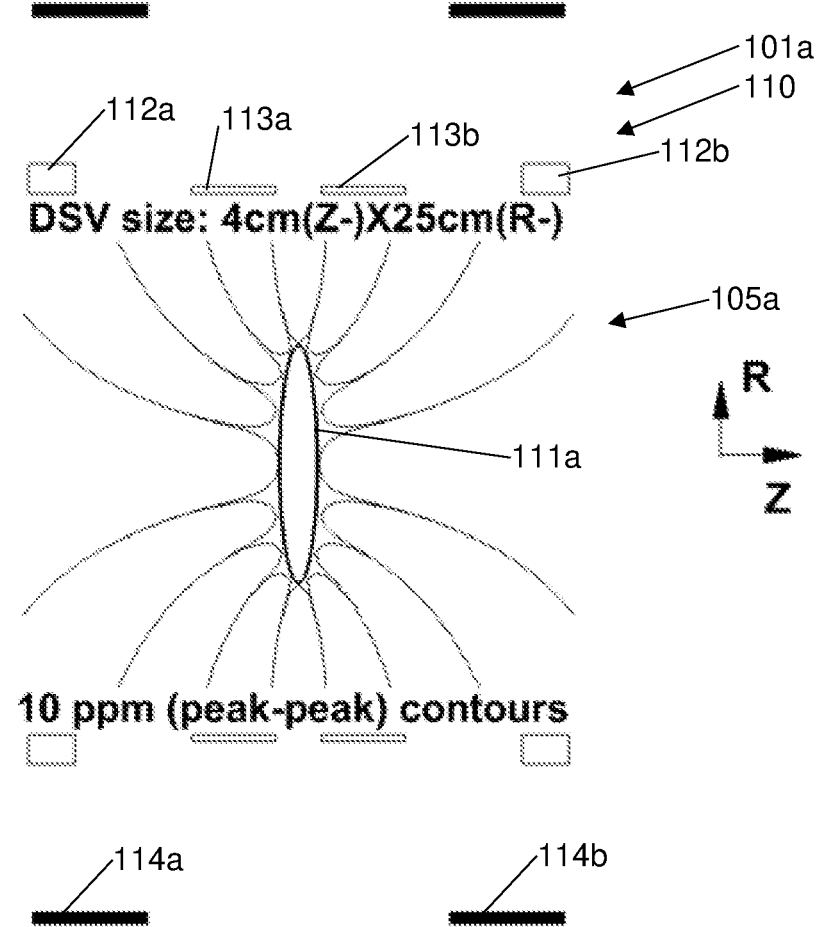
FIG. 1A illustrates a magnet coil configuration and DSV dimensions of the magnetic resonance imaging system of FIG. 1.
Figure 1B:
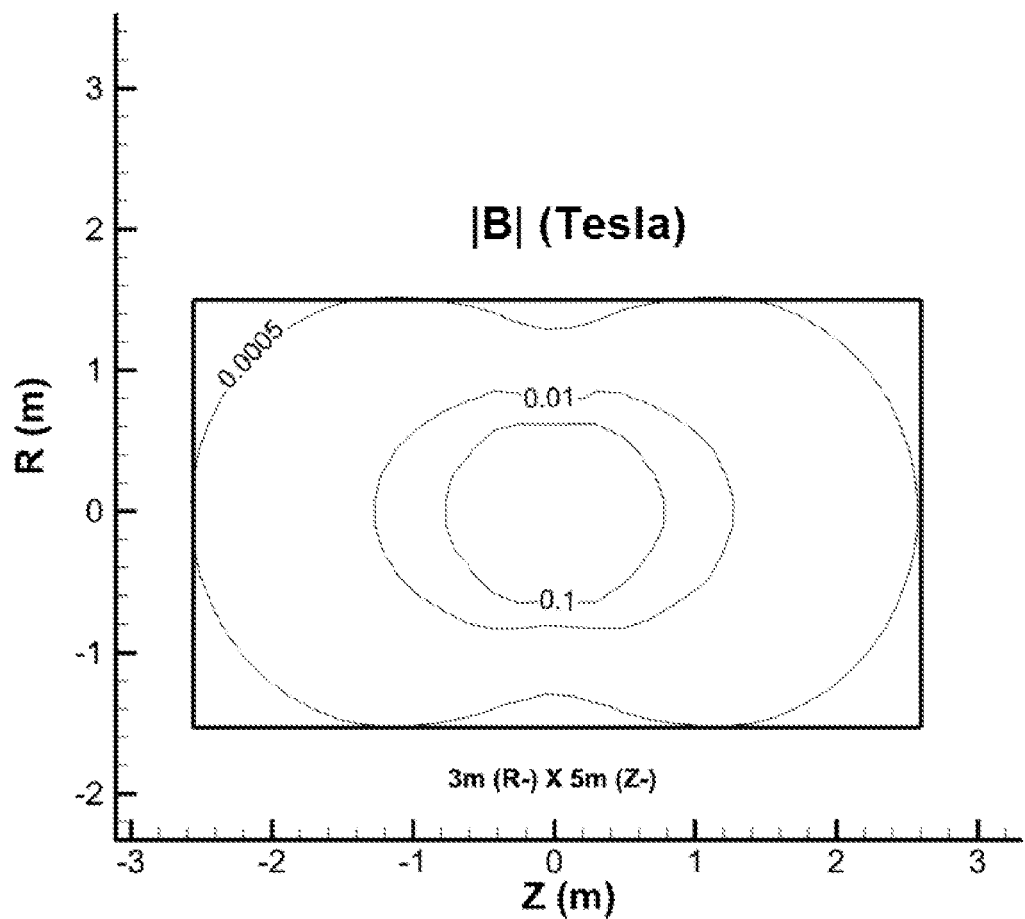
FIG. 1B illustrates the stray field outside the magnet and the 5 Gauss line of the magnetic resonance imaging system of FIG. 1.

FIGS. 1A and 1B respectively illustrate the magnet configuration and DSV, and the 5 Gauss lines of the 1.5 Tesla superconducting magnet 101a.

Superconducting magnet 101a has the same primary coil structure 110 as superconducting magnet 101. As shown, the size of the DSV 111a is 250 mm (X−)×250 mm (Y−)×40 mm(Z−), providing a dimensional ratio of $Dz_1/Dr_1$ of 40 mm/250 mm which is equal to 0.16, and peak to peak homogeneity of 10 ppm.

The bore 105a of the magnet 101a has a cold bore length of 570 mm and an inner bore diameter of 570 mm.

The respective end coils 112a, 112b, located at opposite ends of the bore 105a are spaced apart by 520 mm.

Referring to FIG. 1B, the size of the 5 Gauss line is 3 meters in the radial direction and 5 meters in the axial direction, which demonstrates well controlled stray fields.

Figure 2:
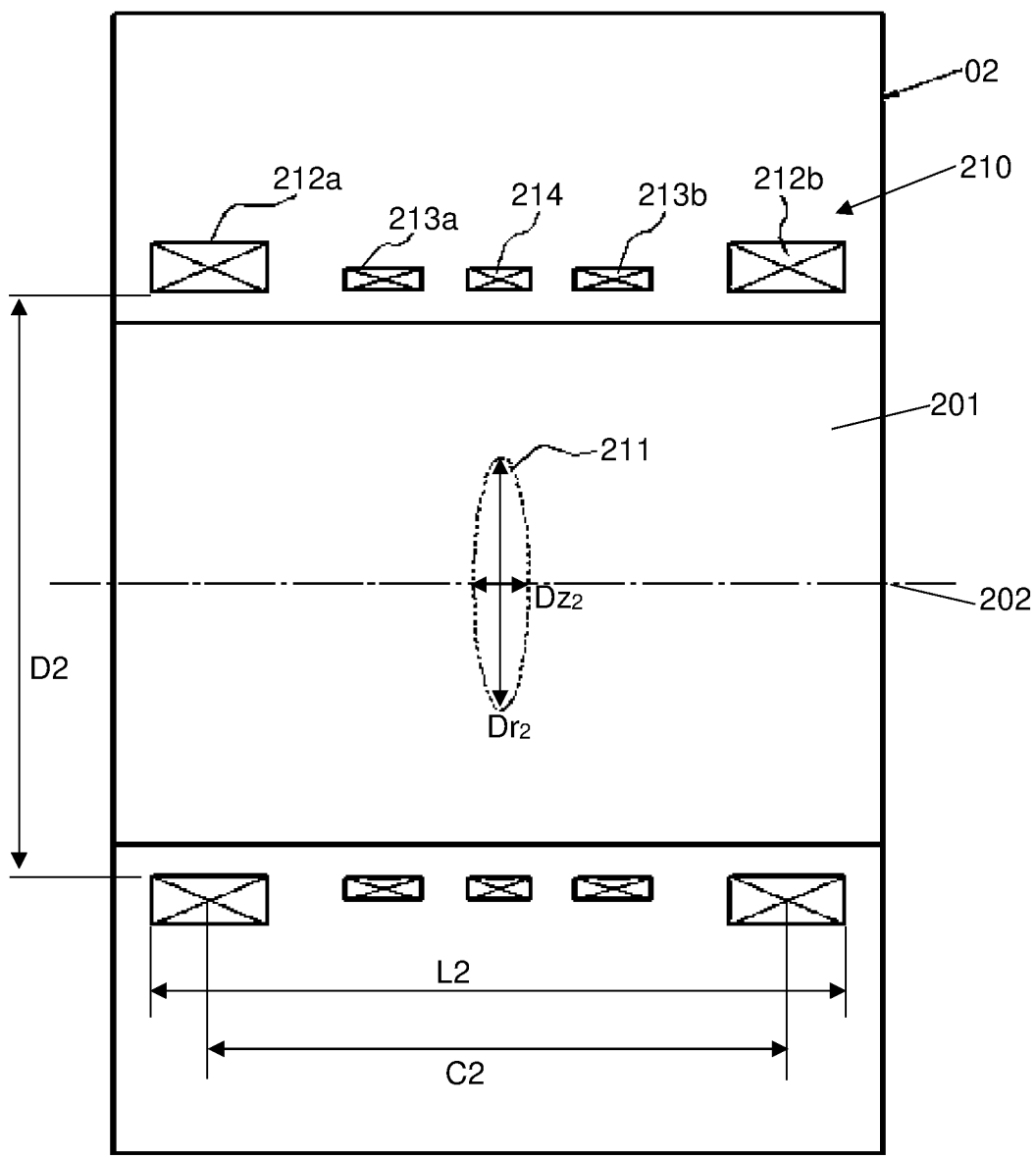
FIG. 2 illustrates a schematic cross-section view of a magnet for use in a magnetic resonance imaging system according to a second embodiment of the present invention.

Turning now to FIG. 2, there is shown a superconducting magnet 02 suitable for use in a magnetic resonance imaging system having a primary coil structure 210 according to an embodiment of the present invention.

The magnet 02 includes a bore 201 extending axially through the magnet 02 parallel to longitudinal axis 202.

The bore 201 of the magnet 02 has a cold bore length L2 (preferably between 250 mm and 1000 mm) and an inner bore diameter D2.

The primary coil structure 210 of the magnet 02 includes five primary coils: a first end coil 212a, a second end coil 212b, and three intermediate coils 213a, 213b and 214 arranged symmetrically with respect to the centre of DSV 211, with intermediate coil 214 spanning over the centre of the DSV 211. The first end coil 212a and the second end coil 212b are spaced apart by distance C2, which is preferably between 300 mm and 1000 mm.

All of the five coils 212a, 212b, 213a, 213b and 214 of the primary coil structure 210 have the same polarity, producing the disk-type DSV 211 having an axial diameter $Dz_2$ less than the radial diameter $Dr_2$, where the ratio of the axial diameter $Dz_2$ to the radial diameter $Dr_2$ of the DSV 211 is equal to or less than 0.75.

Figure 3:
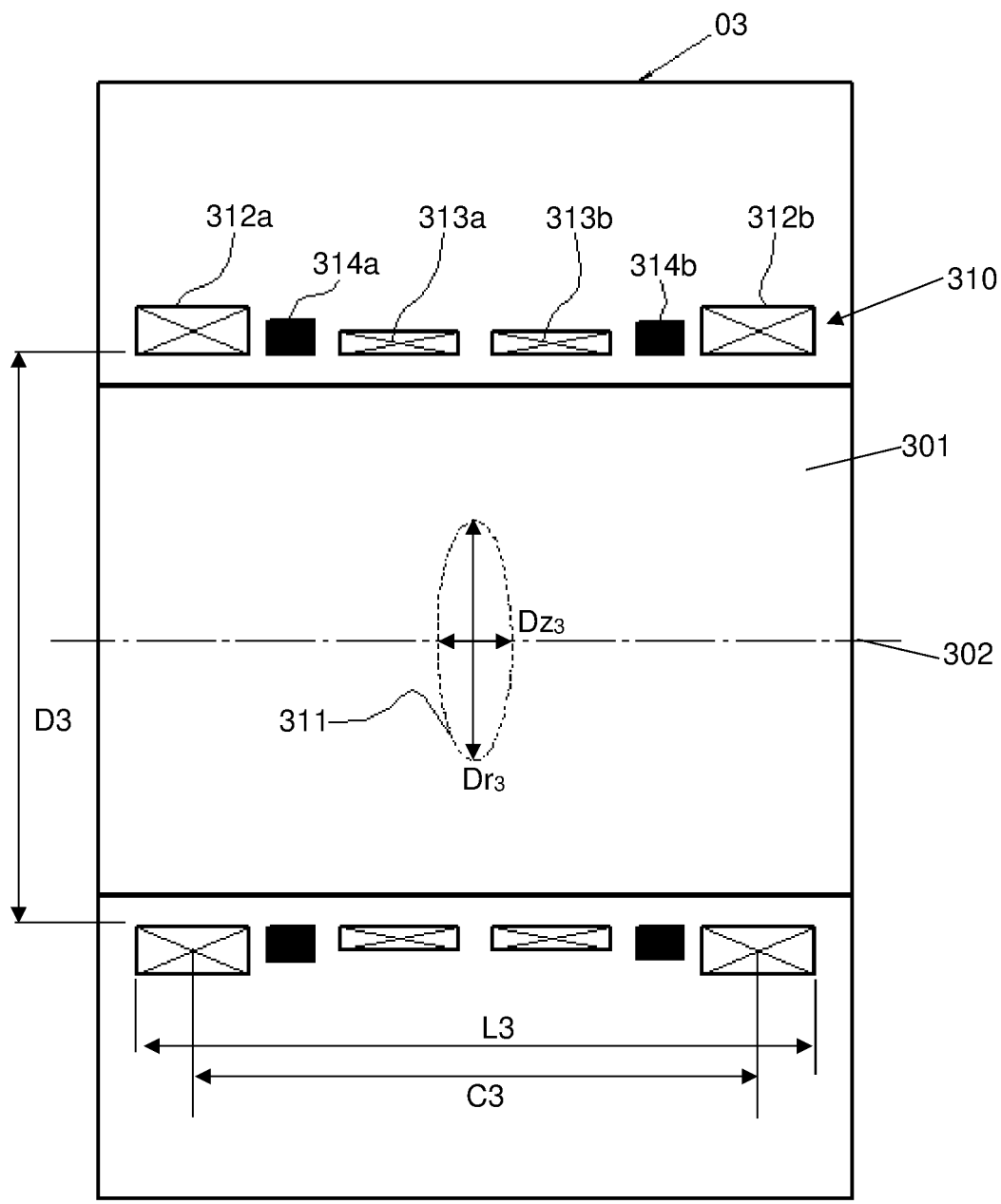
FIG. 3 illustrates a schematic cross-section view of a magnet for use in a magnetic resonance imaging system according to a third embodiment of the present invention.

Referring to FIG. 3, there is shown a superconducting magnet 03 suitable for use in a magnetic resonance imaging system, the magnet 03 having a primary coil structure 310 according to an embodiment of the present invention.

The magnet 03 includes a bore 301 extending axially through the magnet 03 parallel to longitudinal axis 302.

The magnet 03 has a cold bore length L3 (preferably between 250 mm and 1000 mm) and an inner bore diameter D3.

The primary coil structure 310 includes six primary coils in the magnet 03 distributed symmetrically over the centre of DSV, four of which 312a, 312b, 313a, 313b have the same polarity. The remaining two coils 314a and 314b have an opposite polarity to the other four which produces disk-type DSV 311 having an axial diameter $Dz_3$ less than the radial diameter $Dr_3$, where the ratio of the axial diameter $Dz_3$ to the radial diameter $Dr_3$ of the DSV 211 is equal to or less than 0.75.

The respective end coils 312a, 312b, located at opposite ends of the bore 301 are spaced apart by distance C3, which is preferably between 300 mm and 1000 mm. It will be appreciated that the distance between the end coils 312a, 312b is measured from a centre of one coil to a centre of the other coil.

Figure 3A:
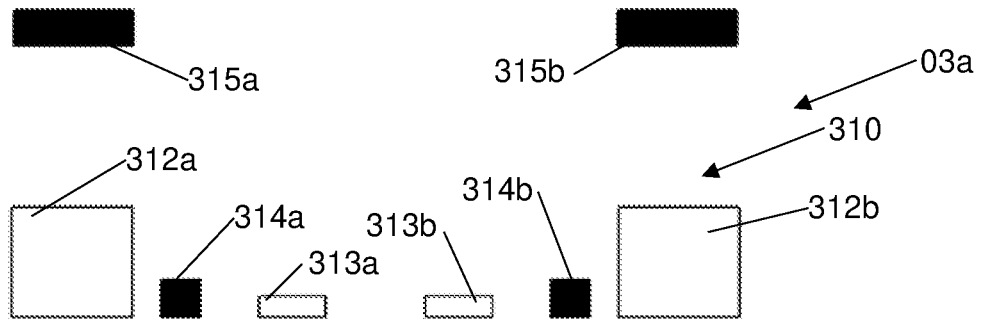
FIG. 3A illustrates a magnet coil configuration and DSV dimensions of the magnetic resonance imaging system of FIG. 3.
Figure 3A:
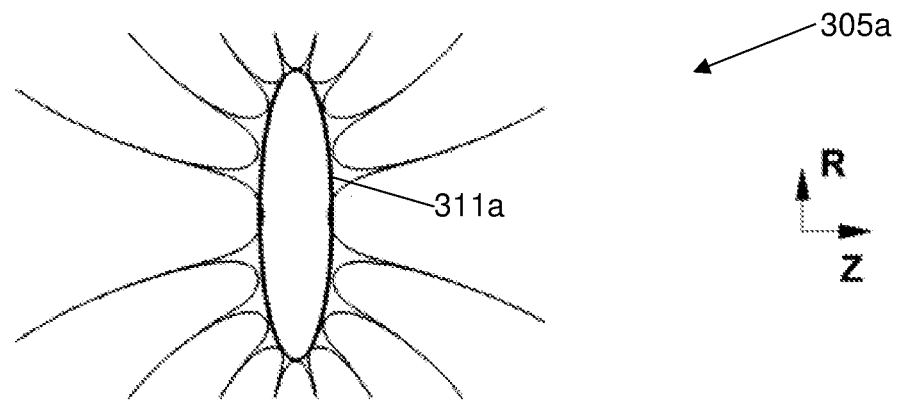
Figure 3A:
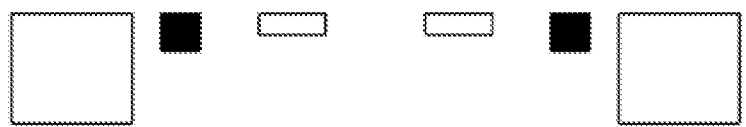
Figure 3B:
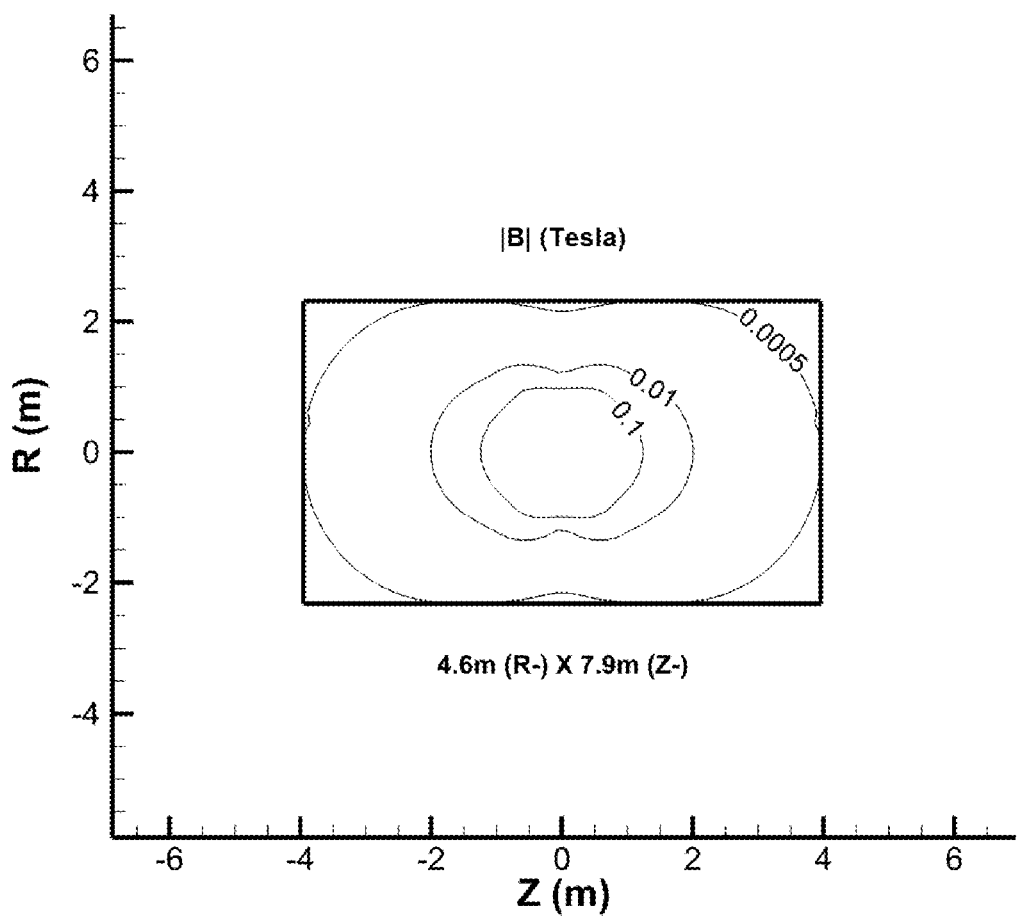
FIG. 3B illustrates the stray field outside the magnet and the 5 Gauss line of the magnetic resonance imaging system of FIG. 3.

FIGS. 3A and 3B illustrate the magnet configuration and DSV, and the 5 Gauss lines of the 3.0 Tesla superconducting magnet 03a, which is substantially the same as superconducting magnet 03 having the same primary coil structure 310.

As mentioned above, the magnet 03 (and thus magnet 03a) employs six primary coils 312a, 312b, 313a, 313b, 314a, 314b in which four primary coils 312a, 312b, 313a, 313b have positive polarity and two primary coils 314a, 314b have negative polarity. In addition, magnet 03a includes two shield coils 315a, 315b also having a negative polarity.

The dimensions of the DSV 311a, shown in FIG. 3A are 320 mm (X−)×320 mm (Y−)×100 mm (Z−). This provides a dimension ratio of 0.3125 ($Dz_3/Dr_{3=100}$ mm/320 mm) and peak to peak contours of 10 ppm.

The bore 305a of the magnet 03a has a cold bore length of 800 mm and an inner bore diameter of 760 mm.

The respective end coils 312a, 312b, located at opposite ends of the bore 305a are spaced apart by 667 mm As shown in FIG. 3B, this configuration provides a 5 Gauss line that is 4.6 meters in the radial direction and 7.9 meters in the axial direction, which again demonstrates that the stray fields are well controlled.

Figure 4:
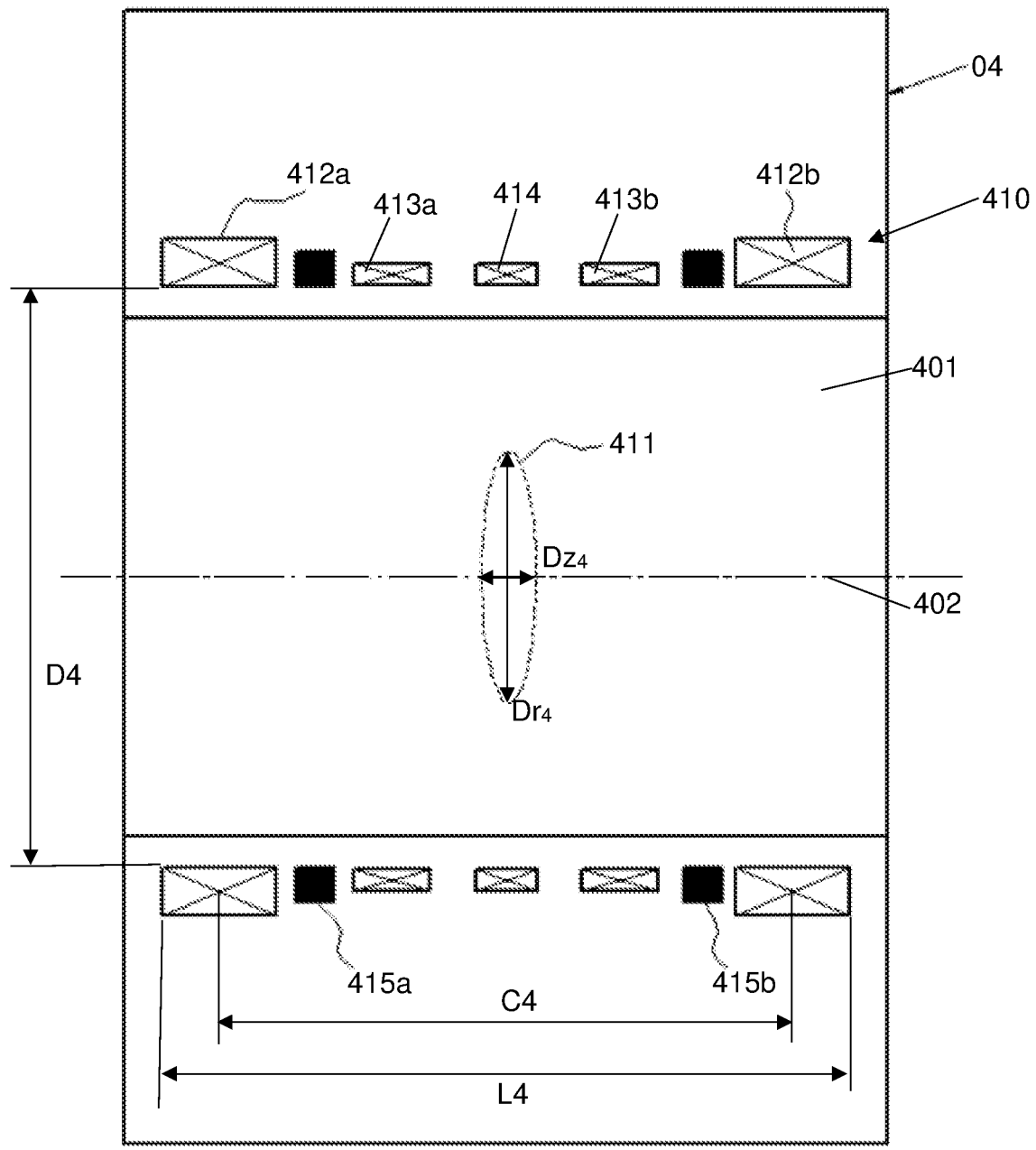
FIG. 4 illustrates a schematic cross-section view of a magnet for use in a magnetic resonance imaging system according to a fourth embodiment of the present invention.

FIG. 4 shows the primary coil structure 410 of the fourth preferred embodiment of the present invention in form of a superconducting magnet 04.

The magnet 04 has a cold bore length L4 (preferably between 250 mm and 1000 mm) and an inner bore diameter D4.

The magnet 04 includes a primary coil structure 410 having seven primary coils: a first end coil 412a, a second end coil 412b, and five intermediate coils 413a, 413b, 414, 415a and 415b.

The primary coil structure 410 is arranged symmetrically with respect to the centre of DSV 411, with coil 414 spanning over the centre of the DSV 411. The first end coil 412a and the second end coil 412b are located at opposing ends of the bore 401 and are spaced apart by distance C4, which is preferably between 300 mm and 1000 mm.

Coils 412a, 412b, 413a, 413b, 414 have the same polarity, while coils 415a and 415b have the opposite polarity, which, in combination, produces the disk-type DSV 411 having an axial diameter $Dz_4$ less than the radial diameter $Dr_4$, where the ratio of the axial diameter $Dz_4$ to the radial diameter $Dr_4$ of the DSV 411 is equal to or less than 0.75.

Figure 4A:
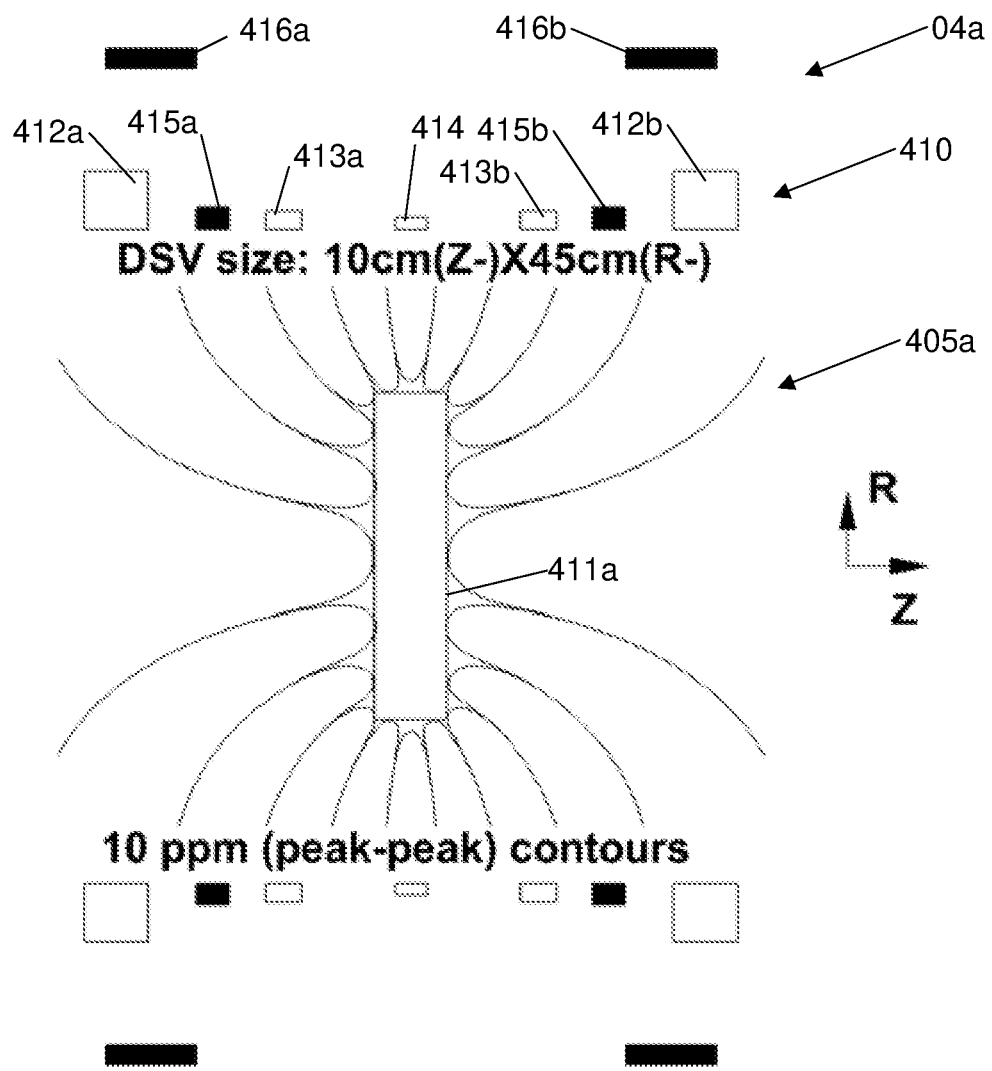
FIG. 4A illustrates a magnet coil configuration and DSV dimensions of the magnetic resonance imaging system of FIG. 4.
Figure 4B:
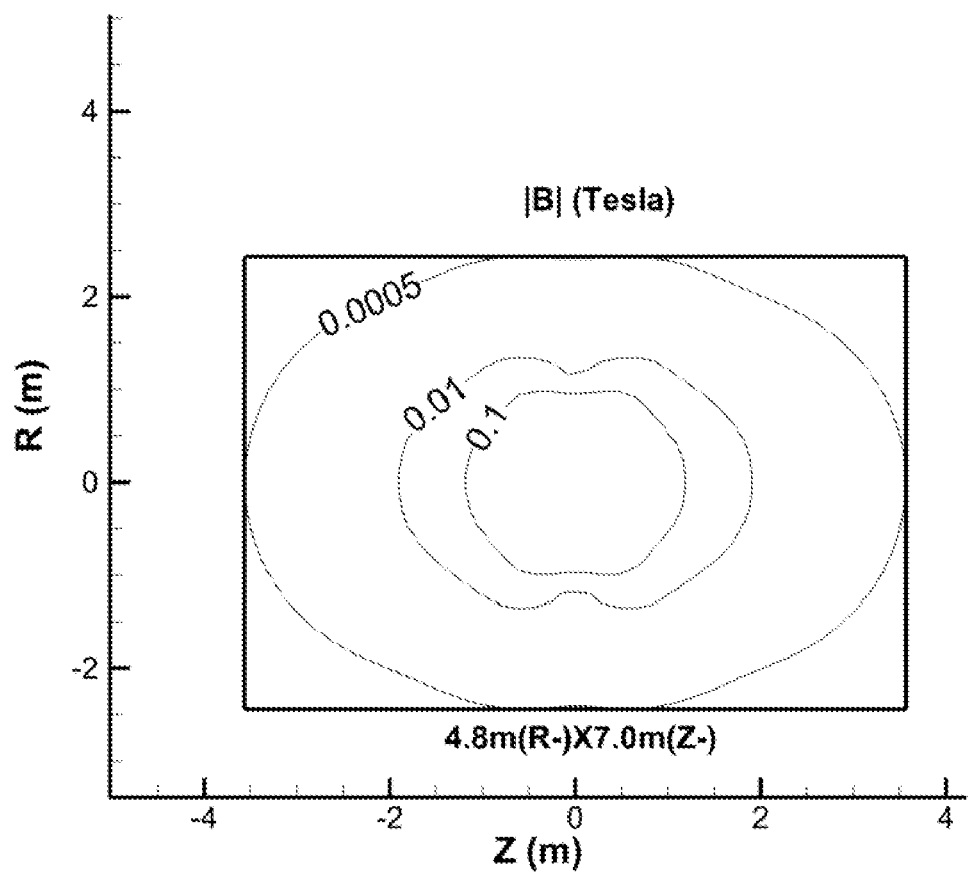
FIG. 4B illustrates the stray field outside the magnet and the 5 Gauss line of the magnetic resonance imaging system of FIG. 4.

FIGS. 4A and 4B illustrate the magnet configuration and DSV, and the 5 Gauss lines of the 1.5 Tesla superconducting magnet 04a, which is substantially the same as superconducting magnet 04 having the same primary coil structure 410.

The magnet 04a employs seven primary coils 412a, 412b, 413a, 413b, 414, 415a, 415b (as in magnet 04) and two shield coils 416a, 416b, in which five primary coils 412a, 412b, 413a, 413b, 414 have positive polarity and two primary coils 415a, 415b as well as the two shield coils 416a, 416b have negative polarity.

The DSV 411a has dimensions of 450 mm (X−)×450 mm (Y−)×100 mm(Z−), providing a dimensional ratio of 0.222 ($Dz_4/Dr_4$=100 mm/450 mm).

The magnet 04a has a cold bore length of 899 mm and an inner bore diameter of 900 mm.

The respective end coils 412a, 412b, located at opposite ends of the bore 405a are spaced apart by 800 mm.

Turning to FIG. 4B, it will be appreciated that the size of the 5 Gauss line is 4.8 meters in the radial direction and 7.0 meters in the axial direction which shows that the stray fields are controlled.

Referring briefly back to FIG. 4A, it should be noted that the DSV 411a has peak to peak homogeneity of 10 ppm.

Figure 5:
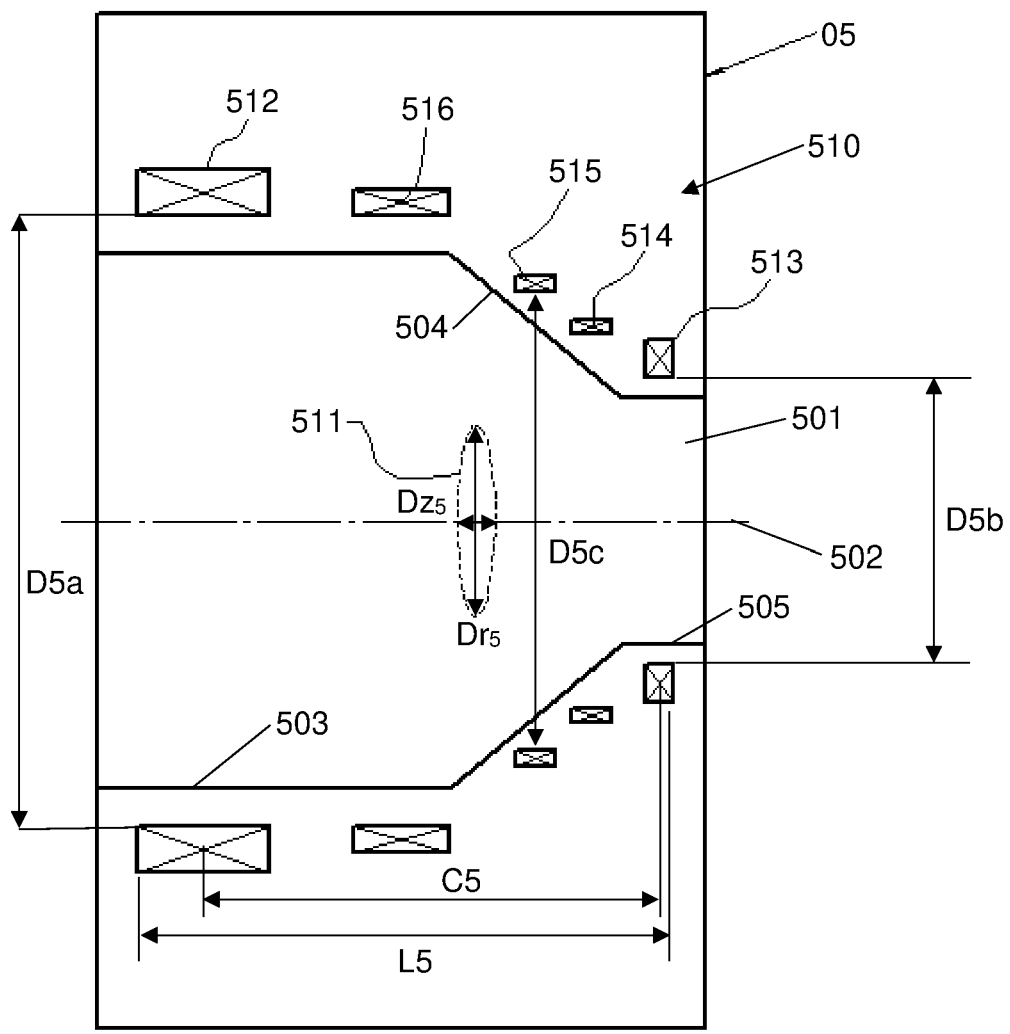
FIG. 5 illustrates a schematic cross-section of a magnet for use in a magnetic resonance imaging system according to a fifth embodiment of the present invention.

FIG. 5 shows the primary coil structure 510 of superconducting magnet 05.

The magnet 05 includes a frustoconical bore 501 extending axially through the magnet 05 about longitudinal axis 502.

The magnet 05 includes a primary coil structure 510 having five primary coils: a first end coil 512, a second end coil 513, and three intermediate coils 514, 515 and 516 located between the first end coil 512 and the second end coil 513. All of the coils 512-516 are of the same polarity, having an asymmetric, frustoconical arrangement. The bore 501 of the magnet 05 has a cold bore length L5 (preferably between 250 mm and 1000 mm). The first end coil 512a and the second end coil 513 are spaced apart by distance C5, which is preferably between 300 mm and 1000 mm.

The end coil 512 has the largest inner diameter D5a about cylindrical portion 503, while another end coil 513 has the smallest inner diameter D5b about cylindrical portion 505 which is significantly smaller than that of end coil 512. Typically, the coil 516 has a similar inner diameter as that of end coil 512, allowing access for human shoulders. As shown, coils 513, 514 are located about the angled portion/frustoconical portion 504 of the bore 502 having an intermediate inner diameter D5c which is between largest diameter D5a and smaller inner diameter D5b.

The magnet 05 produces disk-type DSV 511 having an axial diameter $Dz_5$ less than the radial diameter $Dr_5$, where the ratio of the axial diameter $Dz_5$ to the radial diameter $Dr_5$ of the DSV 511 is equal to or less than 0.75.

Figure 6:
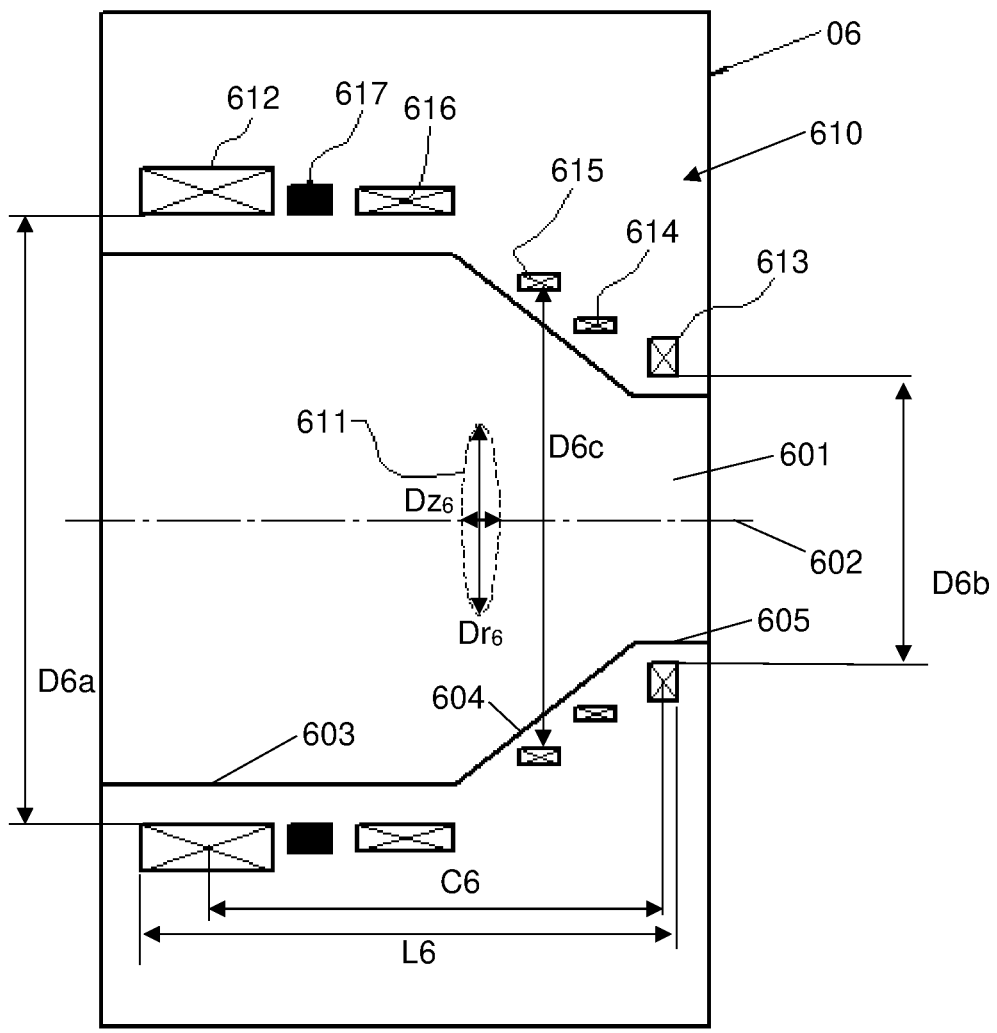
FIG. 6 illustrates a schematic cross-section of a magnet for use in a magnetic resonance imaging system according to a sixth embodiment of the present invention.

FIG. 6 shows the primary coil structure of the sixth preferred embodiment of the present invention, in which the superconducting magnet 06 has a primary coil structure 610.

The magnet 06 includes a narrowing bore 601 extending axially through the magnet 06 about longitudinal axis 602.

The primary coil structure 610 of magnet 06 comprises six primary coils: a first end coil 612, a second end coil 613, and four intermediate coils 614, 615, 616 and 617 located therebetween. The primary coils 612-617 have an asymmetric, frustoconical arrangement. Five coils 612, 613, 614, 615, 616 have the same polarity, while one primary coil 617 adjacent the end coil 612 has an opposing, negative polarity. In some alternative embodiments, the primary coil 617 can be located adjacent end coil 613.

The first end coil 612 and the second end coil 613 are located at opposing ends of the bore 601 and spaced apart by distance C6, which is preferably between 300 mm and 1000 mm. It will be appreciated that the distance between the end coils 612, 613 is measured from a centre of one coil to a centre of the other coil.

The end coil 612 is located about the widest portion (first cylindrical portion 603) of the bore 601 having the largest inner diameter D6a, while the opposing end coil 613 is located about a narrower portion (second cylindrical portion 605) of the bore 601 having the smallest inner diameter D6b which is significantly smaller than that of the largest inner diameter D6a.

As shown, coils 614, 615 are located about the angled portion/frustoconical portion 604 of the bore 601 having an intermediate diameter D6c which is between largest inner diameter D6a and smaller inner diameter D6b.

Typically, the coil 616 has a similar inner diameter to that of end coil 612, allowing access for human shoulders.

The magnet 06 produces disk-type DSV 611 having an axial diameter $Dz_6$ less than the radial diameter $Dr_6$, where the ratio of the axial diameter $Dz_6$ to the radial diameter $Dr_6$ of the DSV 611 is equal to or less than 0.75.

In the illustrated embodiment, the magnet 06 has a cold bore length of L6 (preferably between 250 mm and 1000 mm), a largest inner bore diameter D6a and a smaller inner bore diameter D6b.

Figure 6A:
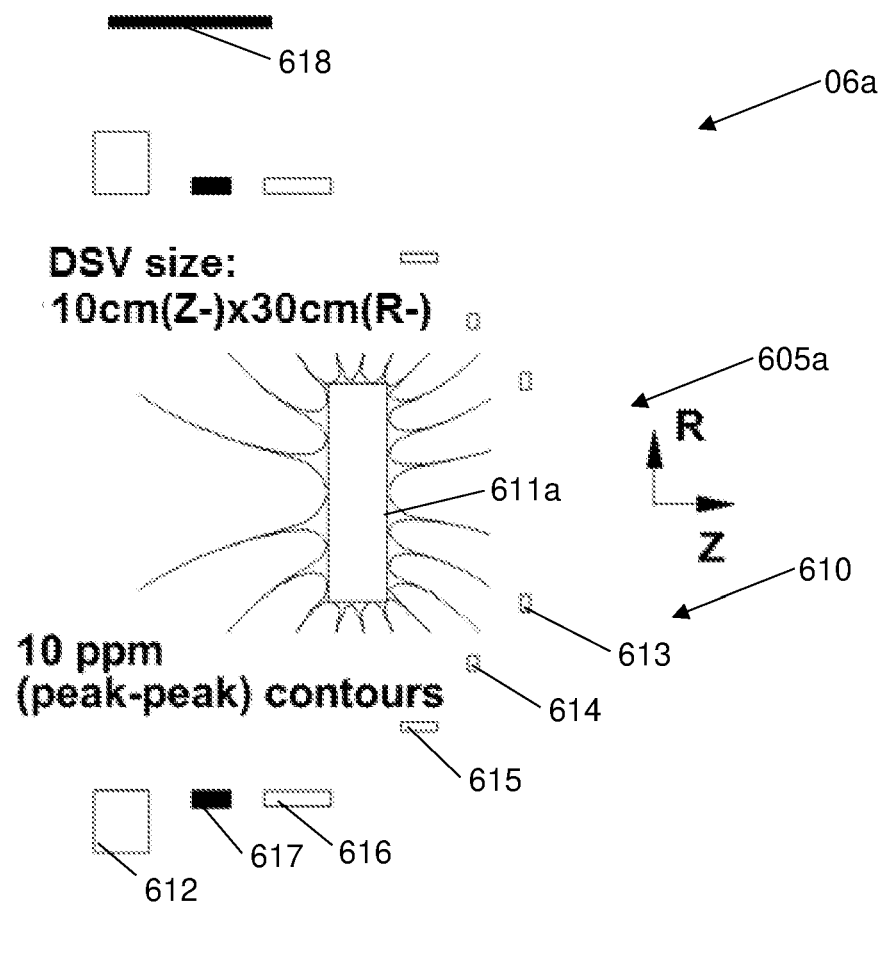
FIG. 6A illustrates a magnet coil configuration and DSV dimensions of the magnetic resonance imaging system of FIG. 6.
Figure 6B:
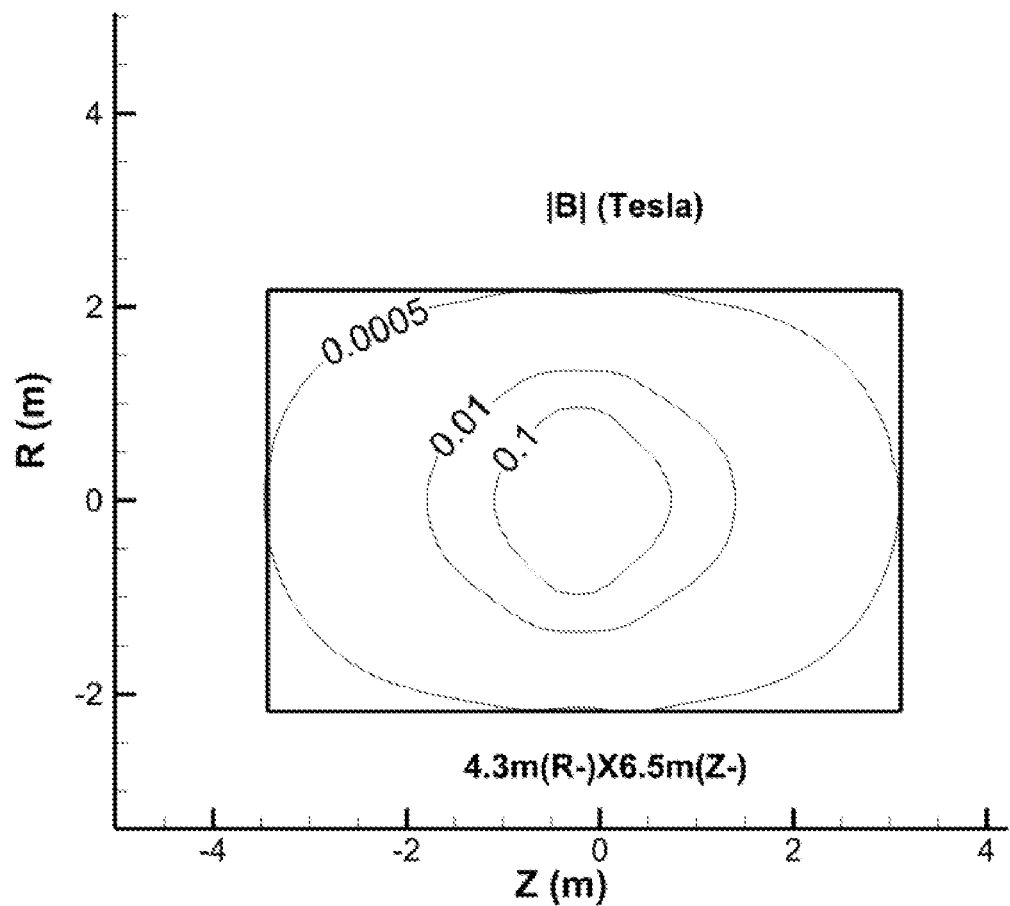
FIG. 6B illustrates the stray field outside the magnet and the 5 Gauss line of the magnetic resonance imaging system of FIG. 6.

FIGS. 6A and 6B illustrate the magnet configuration and DSV, and the 5 Gauss lines of the 1.5 Tesla superconducting magnet 06a, which is substantially the same as superconducting magnet 06 having the same primary coil structure 610. Similar to magnet 06, magnet 06a employs six primary coils 612, 613, 614, 615, 616, 617. Magnet 06a also includes one shield coil 618. Five primary coils 612, 613, 614, 615, 616 have a positive polarity and one primary coil 617 as well as the shield coil 618 have an opposing, negative polarity.

The DSV 611a produced by magnet 06a has dimensions of 300 mm (X−)×300 mm (Y−)×100 mm(Z−) producing a $Dz_6/Dr_6$ ratio of 0.333 (100 mm/300 mm) and peak to peak homogeneity of 10 ppm.

In the illustrated embodiment, the magnet 06a has a cold bore length of 600 mm, a largest inner bore diameter of 820 mm and a smallest inner bore diameter of 282 mm.

The respective end coils 612, 613, located at opposite ends of the bore 605a are spaced apart by 550 mm. With reference to FIG. 6B, it can be seen that the size of the 5 Gauss line of magnet 06a is 4.3 meters in the radial direction and 6.5 meters in the axial direction to show that the stray fields are well controlled.

Figure 7:
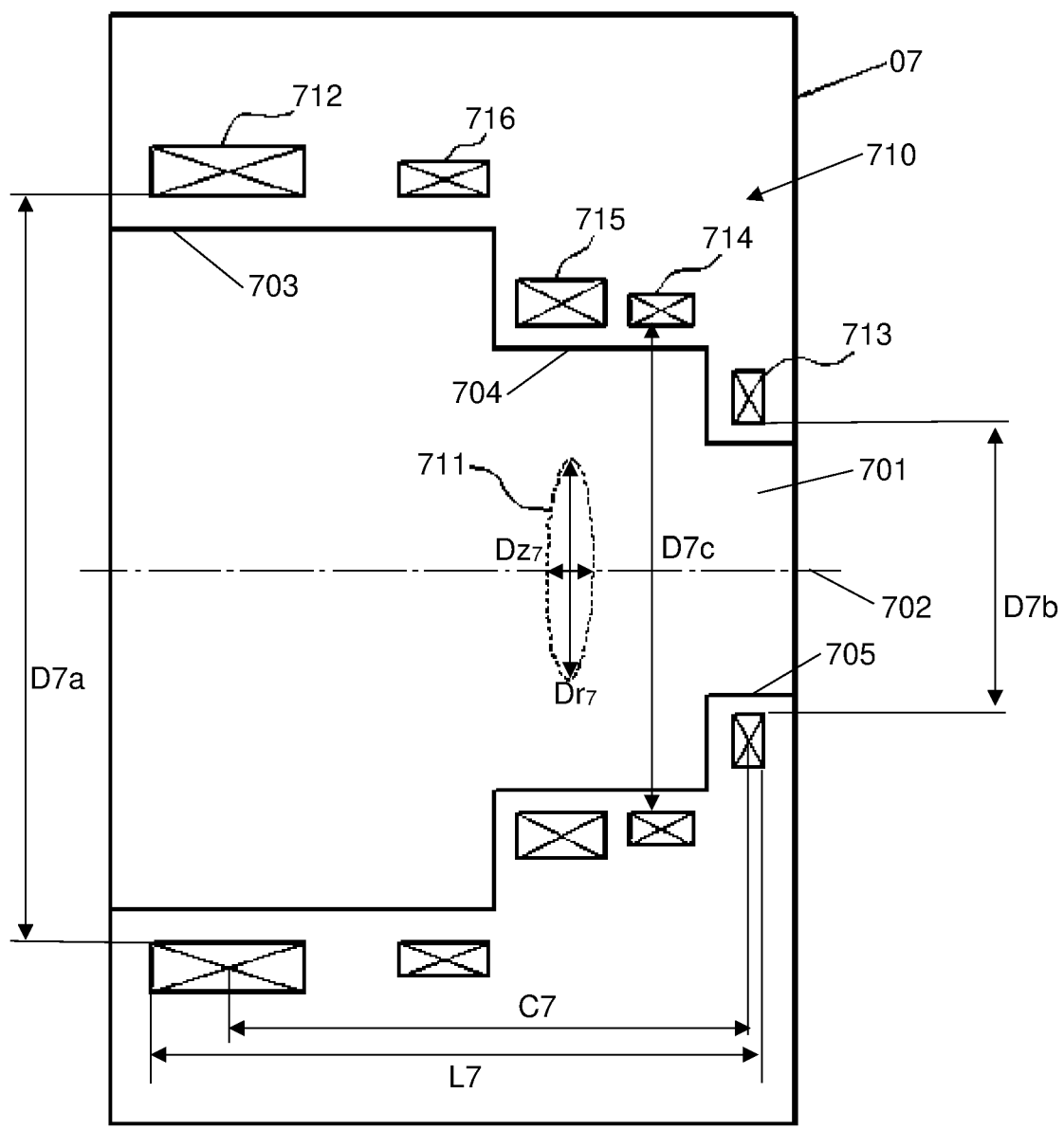
FIG. 7 illustrates a schematic cross-section of a magnet for use in a magnetic resonance imaging system according to a seventh embodiment of the present invention.

FIG. 7 shows another magnet 07 having a primary coil structure 710.

The magnet 07 includes a stepped bore 701 extending axially through the magnet 07 about longitudinal axis 702.

In the illustrated embodiment, the magnet 07 has a cold bore length of L7 (preferably between 250 mm and 1000 mm).

The primary coil structure 710 has five primary coils 712, 713, 714, 715 and 716 of the same polarity, having an asymmetric, three-stepped arrangement.

The end coil 712 is located about the widest portion (first step 703) of the bore 701 having the largest inner diameter D7a, while opposing end coil 713 is located about the narrowest portion (third step 705) of the bore 701 having the smallest inner diameter D7b which is significantly smaller than that largest inner diameter D7a.

The first end coil 712 and the second end coil 713 are spaced apart by distance C7, which is preferably between 300 mm and 1000 mm.

The coil 716 has a similar inner diameter as that of end coil 712, allowing access for human shoulders. The two medium sized coils 714 and 715, adjacent the end coil 713, located about the second step (second step 704) of the bore 701 have the same or similar inner diameter D7c that is significantly smaller than the largest inner diameter D7a and significantly larger than the smallest inner diameter D7b.

The magnet 07 produces disk-type DSV 711 having an axial diameter $Dz_7$ less than the radial diameter $Dr_7$, where the ratio of the axial diameter $Dz_7$ to the radial diameter $Dr_7$ of the DSV 711 is equal to or less than 0.75.

Figure 8:
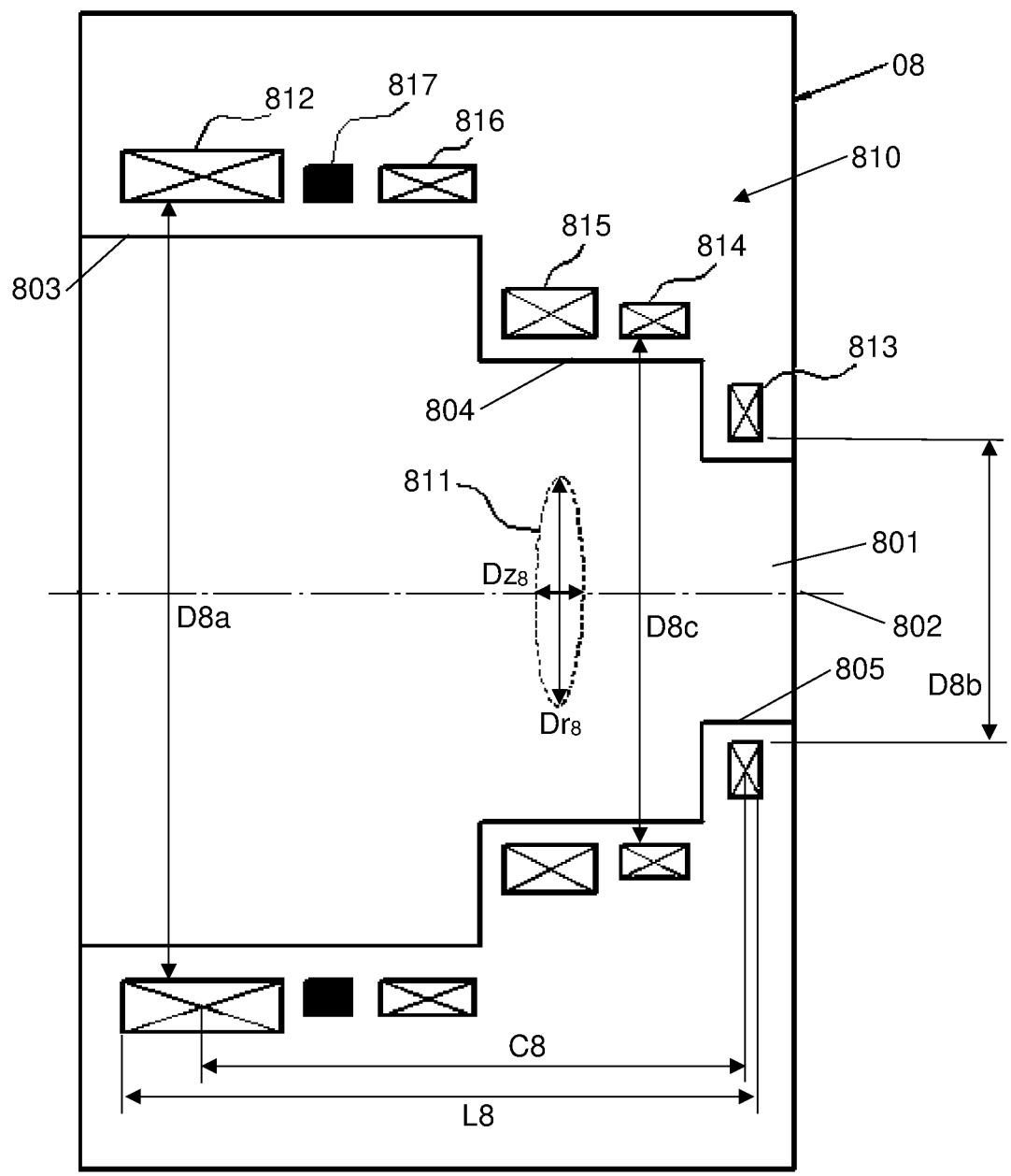
FIG. 8 illustrates a schematic cross-section of a magnet for use in a magnetic resonance imaging system according to an eighth embodiment of the present invention.

FIG. 8 illustrates a primary coil structure 810 of magnet 08.

The magnet 08 includes a stepped bore 801 extending axially through the magnet 08 about longitudinal axis 802.

In the illustrated embodiment, the magnet 08 has a cold bore length of L8 (preferably between 250 mm and 1000 mm).

The primary coil structure 810 comprises six primary coils 812, 813, 814, 815, 816 and 817, having an asymmetric, three-stepped, configuration.

Five coils 812, 813, 814, 815, 816 have the same polarity, while one primary coil 817 adjacent the end coil 812 has an opposing polarity. In some embodiments, primary coil 817 can be located adjacent opposing end coil 813.

The end coil 812 is located about the widest portion (first step 803) of the bore 801 having the largest inner diameter D8a, while opposing end coil 813 is located about the narrowest portion (third step 805) of the bore 801 having the smallest inner diameter D8b which is significantly smaller than the largest inner diameter D8a. Typically the coil 816 has a similar inner diameter to that of end coil 812, allowing access for human shoulders.

The first end coil 812 and the second end coil 81 are spaced apart by distance C8, which is preferably between 300 mm and 1000 mm.

The two medium sized coils 814 and 815, adjacent the end coil 813, located about the second step 804 of the bore 801 have the same or similar inner diameter D8c that is significantly smaller than the largest inner diameter D8a and significantly larger than the smallest inner diameter D8b.

The magnet 08 produces disk-type DSV 811 having an axial diameter $Dz_8$ less than the radial diameter $Dr_8$, where the ratio of the axial diameter $Dz_8$ to the radial diameter $Dr_8$ of the DSV 811 is equal to or less than 0.75.

Figure 9:
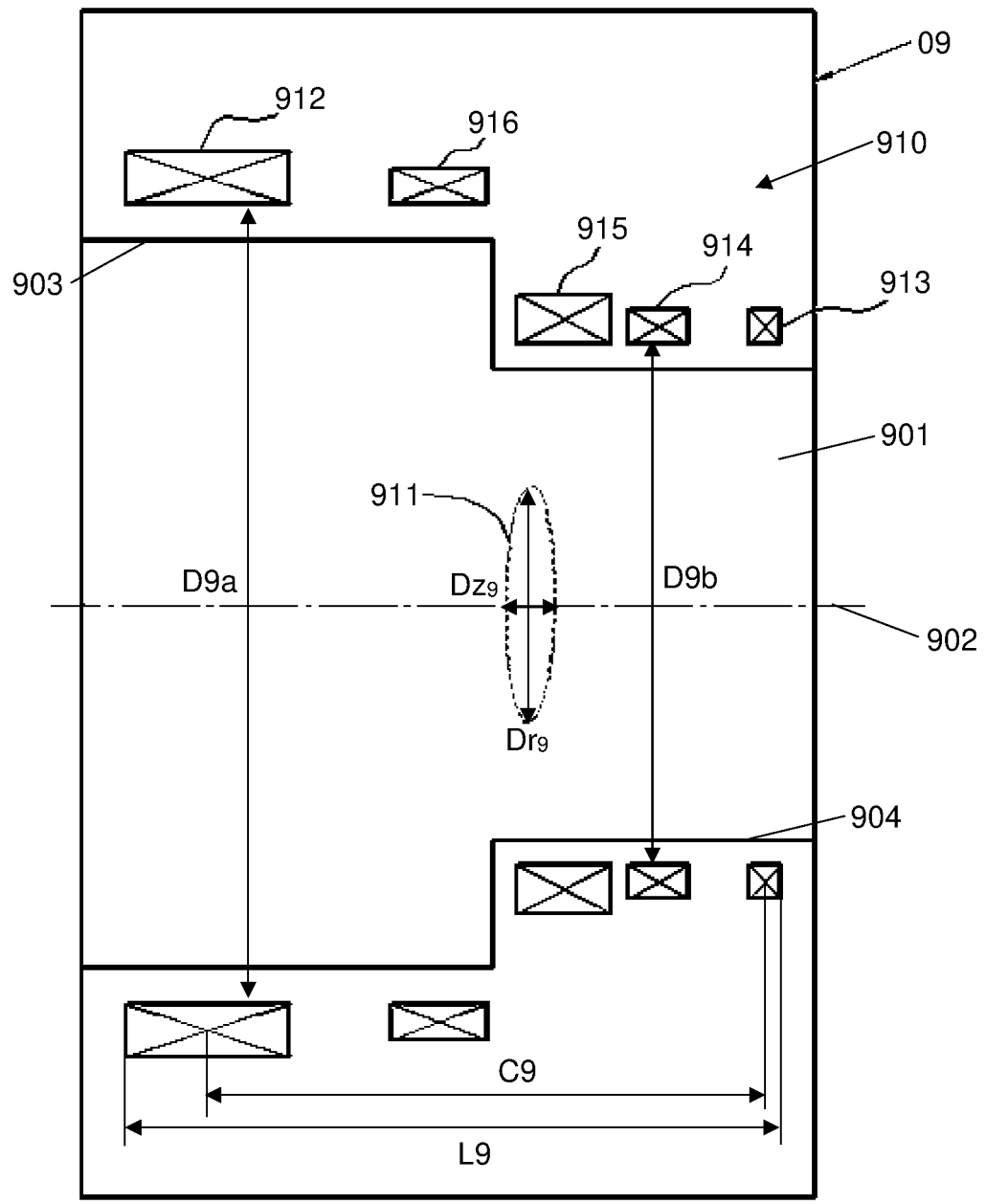
FIG. 9 illustrates a schematic cross-section of a magnet for use in a magnetic resonance imaging system according to a ninth embodiment of the present invention.

FIG. 9 shows a magnet 09 according to another embodiment of the present invention.

The magnet 09 includes a stepped bore 901 extending axially through the magnet 09 about longitudinal axis 902.

In the illustrated embodiment, the magnet 09 has a cold bore length of L9 (preferably between 250 mm and 1000 mm).

The magnet 09 comprises a primary coil structure 910 having five primary coils 912, 913, 914, 915 and 916 of the same polarity, having an asymmetric, two-step arrangement. It will be appreciated that the magnet could have more primary coils.

There are two primary coils 912 and 916 at the first step 903 of the bore 901 that have the same or similar inner diameter D9a. There are also three primary coils 913, 914 and 915 at the second step 904 of the bore 901 that has the same or similar inner diameter D9b.

The inner diameter of coils 912, 916 at the first step 903 is significantly larger than that of coils 913, 914, 915 at the second step 904.

The first end coil 912 and the second end coil 913 are spaced apart by distance C9, which is preferably between 300 mm and 1000 mm.

The magnet 09 produces disk-type DSV 911 having an axial diameter $Dz_9$ less than the radial diameter $Dr_9$, where the ratio of the axial diameter $Dz_9$ to the radial diameter $Dr_9$ of the DSV 911 is equal to or less than 0.75.

Figure 10:
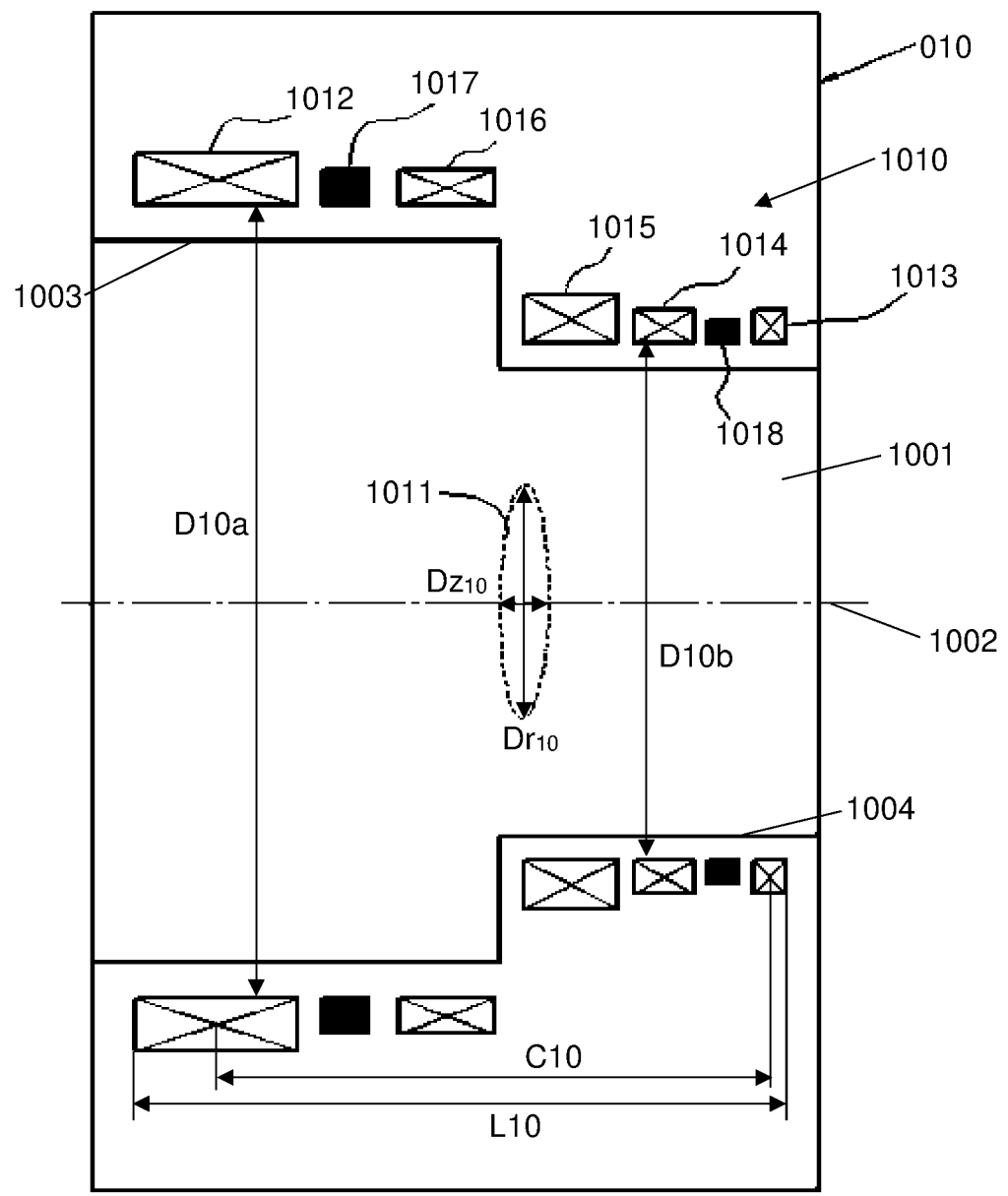
FIG. 10 illustrates a schematic cross-section of a magnet for use in a magnetic resonance imaging system according to a tenth embodiment of the present invention.

FIG. 10 shows a magnet 010 which includes a primary coil structure 1010.

The magnet 010 includes a stepped bore 1001 extending axially through the magnet 010 about longitudinal axis 1002.

In the illustrated embodiment, the magnet 010 has a cold bore length of L10 (preferably between 250 mm and 1000 mm).

The magnet 010 comprises seven primary coils 1012, 1013, 1014, 1015, 1016, 1017 and 1018, having an asymmetric, two-step arrangement. Five coils 1012, 1013, 1014, 1015, 1016 of the primary coil structure 1010 have the same polarity, while the two primary coils 1017, 1018, adjacent the two end coils 1012 and 1013 respectively, have opposite polarities to the five coils 1012, 1013, 1014, 1015, 1016.

The first end coil 1012 and the second end coil 1013 are spaced apart by distance C10, which is preferably between 300 mm and 1000 mm.

There are three primary coils 1012, 1016 and 1017 located about the first step 1003 of the bore 1001 which has an inner diameter D10a. There are also four primary coils 1013, 1014, 1015 and 1018 located about the second step 1004 of the bore 1010 which has an inner diameter D10b.

The inner diameter of coils 1012, 1016, 1017 at the first step 1003 is significantly larger than that of coils 1013, 1014, 1015, 1018 at the second step 1004. The magnet 010 produces disk-type DSV 1011 having an axial diameter $Dz_{10}$ less than the radial diameter $Dr_{10}$, where the ratio of the axial diameter $Dz_{10}$ to the radial diameter $Dr_{10}$ of the DSV 1011 is equal to or less than 0.75.

Figure 11:
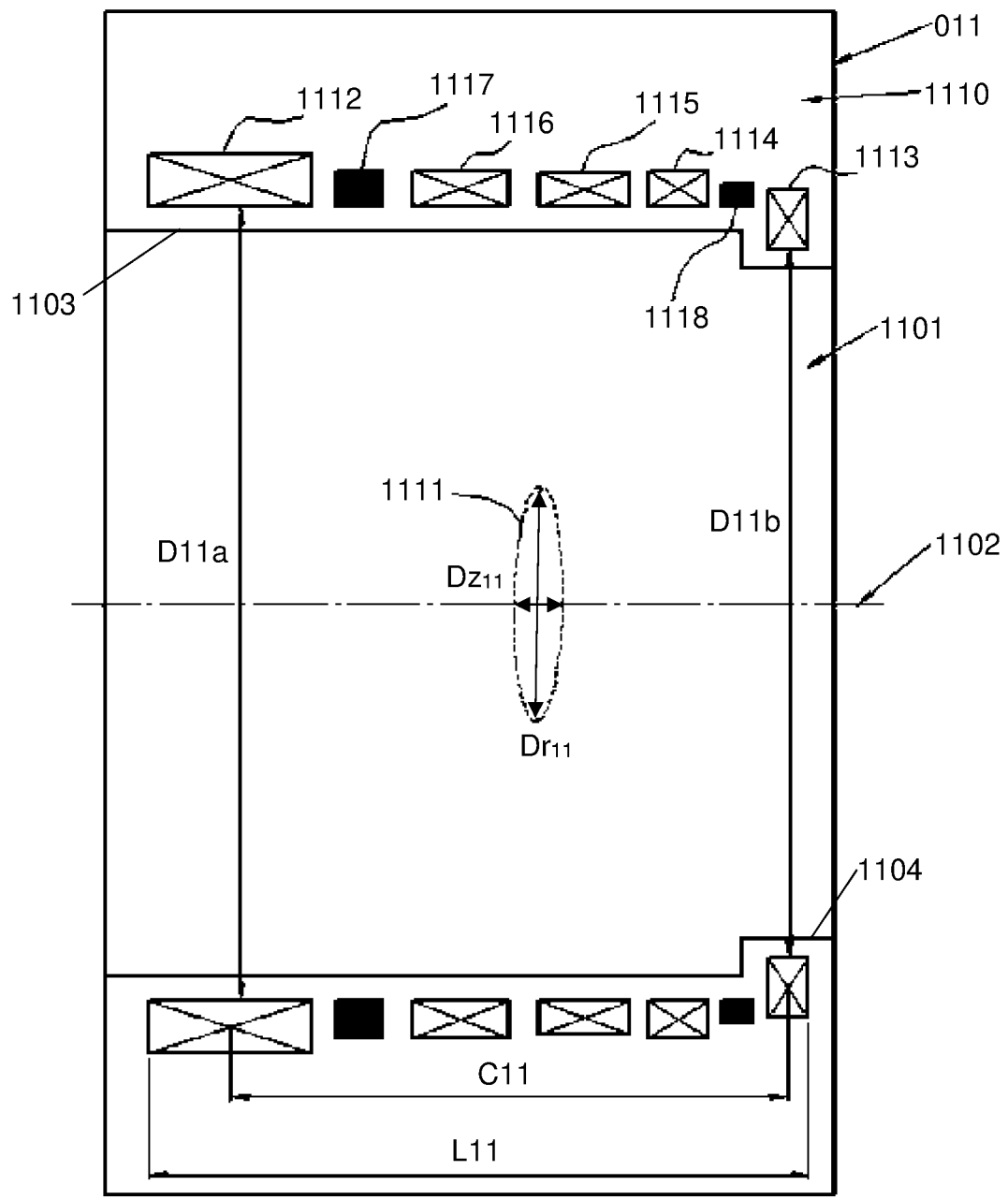
FIG. 11 illustrates a schematic cross-section of a magnet for use in a magnetic resonance imaging system according to an eleventh embodiment of the present invention.

FIG. 11 shows a magnet 011 which includes a primary coil structure 1110.

The magnet 011 includes a two-stepped bore 1101 extending axially through the magnet 011 about longitudinal axis 1102.

In the illustrated embodiment, the magnet 011 has a cold bore length of L11 (preferably between 250 mm and 1000 mm).

The magnet 011 comprises seven primary coils 1112, 1113, 1114, 1115, 1116, 1117 and 1118, having an asymmetric, two-step arrangement.

Five coils 1112, 1113, 1114, 1115, 1116 of the primary coil structure 1110 have the same polarity, while the two primary coils 1117, 1118 adjacent the two end coils 1112 and 1113 respectively, have opposite polarities to the other five coils 1112, 1113, 1114, 1115, 1116.

The first end coil 1112 and the opposing second end coil 1113 are spaced apart by distance C11, which is preferably between 300 mm and 1000 mm.

There are six primary coils 1112, 1114, 1115, 1116, 1117 and 1118 located about the first step 1103 of the bore 1101 which has an inner diameter D11a. The remaining primary coil 1113 is located about the second step 1104 of the bore 1110 which has an inner diameter D11b.

The inner diameter of coils 1112, 1114, 1115, 1116, 1117 and 1118 about the first step 1103 is significantly larger than that of coil 1113 about the second step 1104.

The magnet 011 produces disk-type DSV 1111 having an axial diameter $Dz_{11}$ less than the radial diameter $Dr_{11}$, where the ratio of the axial diameter $Dz_{11}$ to the radial diameter $Dr_{11}$ of the DSV 1111 is equal to or less than 0.75.

With reference to the embodiments above, an inner diameter of the bore is preferably between 200 mm and 1100 mm. In some preferred embodiments, the bore is frustoconical having a largest inner diameter of 820 mm and a smallest inner diameter of 282 mm.

Conventionally, the DSV in an MRI magnet is designed to encompass the whole organ under study (for example, the whole brain). Typical DSV sizes are 45-50 cm in diameter having spherical or slightly ellipsoidal volumes such that the patient remains positioned at the centre of the DSV while the organ is scanned/imaged. Thus the patient is not moved during the examination of that organ. The size of the DSV in the axial direction has a strong influence on the length of the magnet. It is a feature of this invention that the DSV has a much smaller axial extent than its radial extent. This allows the magnet to be shorter than conventional systems and, in use, whole organ imaging is achieved by moving the patient in an automatically controlled fashion through the magnet system. This new approach substantially reduces the DSV restriction from the magnet design and allows a range of novel magnets to be designed. Furthermore, in some embodiments, the patient can be moved through the imaging region/DSV, thereby allowing the length of the imaging device to be significantly shorter as the organ of the patient that is to be imaged does not need to be centred within the DSV.

In use, the magnet is capable of producing a magnetic field of at least 1.0 Tesla, and preferably at least 3.0 Tesla, which is substantially homogeneous over a predetermined imaging region or volume (also called the 'homogeneous region' or DSV'). Typically, the imaging region has an external surface defined by a computed variation of the longitudinal magnetic field relative to the longitudinal magnetic field at the imaging centre of less than 20 parts per million peak-to-peak.

In this specification, the terms "diameter of spherical volume", "DSV" and "imaging region" are used interchangeably.

In this specification, adjectives such as first and second, left and right, top and bottom, and the like may be used solely to distinguish one element or action from another element or action without necessarily requiring or implying any actual such relationship or order. Where the context permits, reference to an integer or a component or step (or the like) is not to be interpreted as being limited to only one of that integer, component, or step, but rather could be one or more of that integer, component, or step, etc.

The above detailed description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention.

In this specification, the terms 'comprises', 'comprising', 'includes', 'including', or similar terms are intended to mean a non-exclusive inclusion, such that a method, system or apparatus that comprises a list of elements does not include those elements solely, but may well include other elements not listed.

Throughout the specification and claims (if present), unless the context requires otherwise, the term "substantially" or "about" will be understood to not be limited to the specific value or range qualified by the terms.

What is claimed is:

1. A magnet suitable for use in a Magnetic Resonance Imaging (MM) system, the magnet having a magnet body having a bore extending therethrough along an axis of the body, the magnet comprising:
a primary coil structure having at least four primary coils positioned along the axis, including a first end coil adjacent a first end of the bore of the magnet and a second end coil adjacent a second end of the magnet,
wherein a largest inner bore diameter of the primary coil structure is greater than 700 mm,
wherein the first end coil and the second end coil are spaced apart by no more than 1000 mm,
wherein an imaging region produced by the primary coils is of a disk-type,
wherein the disk-type imaging region has an axial diameter and a radial diameter, and
wherein the axial diameter is less than the radial diameter, wherein the radial diameter is greater than 200 mm, and
wherein a ratio of the axial diameter to the radial diameter of the disk-type imaging region is equal to or less than 0.60.

2. The magnet according to claim 1, wherein:
a diameter of the imaging region along an x-axis is between 200 mm and 500 mm;
a diameter of the imaging region along a y-axis is between 200 mm and 500 mm; and
a diameter of the imaging region along a z-axis is between 20 mm and 350 mm.

3. The magnet according to claim 1, wherein the imaging region has dimensions of 250 mm(x-)×250 mm(y-)×40 mm(z-) or the imaging region has dimensions of 320 mm(x-)×320 mm(y-)×100 mm(z-) or the imaging region has dimensions of 450 mm(x-)×450 mm(y-)×100 mm(z-) or the imaging region has dimensions of 300 mm(x-)×300 mm(y-)×100 mm(z-).

4. The magnet according to claim 1, wherein the first end coil and the second end coil are spaced apart by between 300 mm and 1000 mm.

5. The magnet according to claim 1, wherein the primary coil structure has between four primary coils and eight primary coils, and wherein each of the primary coils has a same current polarity or wherein one of the between four primary coils and eight primary coils adjacent the second end coil has an opposite current polarity to the second end coil.

6. The magnet according to claim 1, wherein the magnet body and bore are cylindrical, conical, frustoconical or stepped and/or the primary coils are cylindrical, conical, frustoconical or stepped.

7. The magnet according to claim 6, wherein the magnet body and bore comprise at least one cylindrical portion and wherein a cylindrical portion adjoins a frustoconical portion or wherein a first cylindrical portion having a diameter adjoins a second cylindrical portion having a diameter, wherein the diameter of the first cylindrical portion is greater than the diameter of the second cylindrical portion.

8. The magnet according to claim 1, wherein a plurality of frustoconical portions and/or cylindrical portions define a stepped-diameter bore, and at least one primary coil of the primary coil structure is located about a first step of the stepped diameter bore and at least one primary coil of the primary coil structure is located about a second step of the stepped diameter bore.

9. The magnet according to claim 1, wherein an inner diameter of the bore is between 700 mm and 1100 mm, and wherein a length of the bore is between 250 mm and 1000 mm.

10. The magnet according to claim 1, wherein the magnet is capable of producing a magnetic field of at least 1.0 Tesla or the magnet is capable of producing a magnetic field of at least 3.0 Tesla.

11. The magnet according to claim 1, wherein the magnetic field is substantially homogenous over a predetermined imaging region, and wherein the imaging region has an external surface defined by a computed variation of a longitudinal magnetic field relative to the longitudinal magnetic field at an imaging centre of less than 20 parts per million peak-to-peak.

12. The magnet according to claim 1, wherein the magnet further comprises a shield coil structure and the shield coil structure is located around the primary coil structure, wherein the shield coil structure comprises at least one shield coil having a greater diameter than the primary coils and wherein the shield coil structure is located radially outwardly of the primary coil structure, and wherein the shield coil structure comprises at least two shield coils and each of the shield coils carry current in a direction opposite to a direction of current in the first and second end coils of the primary coil structure and wherein each of the shield coils are superconducting or ferromagnetic.

13. The magnet according to claim 1, wherein the magnet further comprises a gradient coil structure comprising a primary coil layer and a shield coil layer, and wherein a length of the primary coil layer of the gradient coil structure is less than a length of the shield coil layer of the gradient coil structure, wherein the gradient coil structure is located within a gradient body located within the magnet body and the gradient body is located between the bore and the magnet body.

14. The magnet according to claim 13, wherein the magnet further comprises one or more Radio Frequency (RF) coils located between the gradient coil structure and the bore, wherein the one or more RF coils are frustoconical and/or cylindrical confirming to a shape of the bore and the RF coils are located on an inner surface of the gradient body surrounding the bore.

15. The magnet according to claim 1, wherein the magnet further comprises one or more shim pockets, each having a shim portion of ferrous or ferromagnetic material located therein, and wherein the shim pockets are frustoconical and/or cylindrical, wherein each primary coil has an associated shim pocket and shim portion having a shape conforming to the shape of the magnet body and/or the bore, wherein the one or more shim portions passively shim the imaging region to achieve a preferred field ($B_0$) homogeneity level and the shim portion is located between the primary coil structure and the shield coil structure, and the shim portion is located outside of the shield coil structure.

16. The magnet according to claim 1, wherein a size of a five Gauss line is between 1.5 m and 6 m in a radial direction and between 2.5 m and 9 m in an axial direction or the five Gauss line has dimensions of:
   3 m in the radial direction and 5 m in the axial direction; or
   4.6 m in the radial direction and 7.9 m in the axial direction; or
   4.8 m in the radial direction and 7.0 m in the axial direction; or
   4.3 m in the radial direction and 6.5 m in the axial direction.

17. A method of magnetic resonance imaging scanning, the method comprising the steps of:
   moving a platform bearing a patient through a magnetic resonance imaging system, the magnet resonance imaging system having a magnet in accordance with claim 1.

18. A magnetic resonance imaging (MM) system having a magnet, the magnet having
   a bore extending along an axis of the magnet, the magnet comprising:
   a primary coil structure having at least four primary coils positioned along the axis, including a first end coil adjacent a first end of the bore of the magnet and a second end coil adjacent a second end of the magnet,
   wherein a largest inner bore diameter of the primary coil structure is greater than 700 mm,
   wherein the first end coil and the second end coil are spaced apart by no more than 1000 mm, and
   wherein an imaging region produced by the primary coils is of a disk-type,
      wherein the disk-type imaging region has an axial diameter and a radial diameter, and
   wherein the axial diameter is less than the radial diameter, wherein the radial diameter is greater than 200 mm, and
   wherein a ratio of the axial diameter to the radial diameter of the disk-type imaging region is equal to or less than 0.60.

19. The magnetic resonance imaging system according to claim 18, wherein the magnetic resonance imaging system comprises a movable platform or portion adapted to support a patient.

20. The magnetic resonance imaging system according to claim 19, wherein the movable platform or portion is adapted to move through the bore of the magnetic resonance imaging system.

* * * * *